(12) United States Patent
Wieder

(10) Patent No.: US 7,749,962 B2
(45) Date of Patent: Jul. 6, 2010

(54) ALPHA 5 BETA 1 AND ITS ABILITY TO REGULATE THE CELL SURVIVAL PATHWAY

(75) Inventor: Robert Wieder, Westfield, NJ (US)

(73) Assignee: University of Medicine & Dentistry of NJ, New Brunswick, NJ (US)

( * ) Notice: Subject to any disclaimer, the term of this patent is extended or adjusted under 35 U.S.C. 154(b) by 45 days.

(21) Appl. No.: 10/521,841

(22) PCT Filed: Jul. 16, 2003

(86) PCT No.: PCT/US03/21954

§ 371 (c)(1),
(2), (4) Date: Jul. 27, 2005

(87) PCT Pub. No.: WO2004/043340

PCT Pub. Date: May 27, 2004

(65) Prior Publication Data

US 2006/0035825 A1    Feb. 16, 2006

Related U.S. Application Data

(60) Provisional application No. 60/396,482, filed on Jul. 16, 2002.

(51) Int. Cl.
*A61K 38/00* (2006.01)

(52) U.S. Cl. ..................... 514/12; 424/130.1

(58) Field of Classification Search .................. None
See application file for complete search history.

(56) References Cited

U.S. PATENT DOCUMENTS

| 5,846,536 A | 12/1998 | Bissell et al. | |
|---|---|---|---|
| 7,311,911 B2 * | 12/2007 | Varner | 424/130.1 |
| 2004/0048312 A1 * | 3/2004 | Li et al. | 435/7.1 |
| 2004/0072775 A1 | 4/2004 | Sobol et al. | |

FOREIGN PATENT DOCUMENTS

WO    WO99/58139    11/1999

OTHER PUBLICATIONS

Bates RC, Lincz LF, Burns GF. Involvement of integrins in cell survival. Cancer Metastasis Rev. Sep. 1995;14(3):191-203.*
Nista A. et al. Functional role of alpha4beta1 and alpha5beta1 integrin fibronectin receptors expressed on adriamycin-resistant MCF-7 human mammary carcinoma cells. Int J Cancer. Jul. 3, 1997;72(1):133-141.*
Zips et al. New Anticancer Agents: In Vitro and In Vivo Evaluation. In Vivo. 19: 1-7, 2005.*
Akamatsu et al. Suppression of Transformed Phenotypes of Human Fibrosarcoma Cells by Overexpression of Recombinant Fibronectin. Cancer Research 56, 4541-4546, Oct. 1, 1996.*
Schreiner et al. Increased Tumorigenicity of Fibronectin Receptor Deficient Chinese Hamster Ovary Cell Variants. Cancer Research 51, 1738-1740, Mar. 15, 1991.*
National Cancer Institute, retrieved on Nov. 9, 2009 at the following web address http://www.cancer.gov/dictionary/?CdrID=45587.*
Korah, et al., Integrin α5β1 Promotes Survival of Growth-Arrested Breast Cancer Cells: An in Vitro Paradigm for Breast Cancer Dormancy in Bone Marrow, *Cancer Research*, 64: 4514-4522 (2004).
Stoeltzing et al., Inhibition of Integrin α5β1 Function with a Small Peptide (ATN-161) Plus Continuous 5-Fu Infusion Reduces Colorectal Liver Metastases and Improves Survival in Mice, *Int. J. Cancer*,104: 496-503 (2003).
Khalili et al., A Non-RGD-based Integrin Binding Peptide (ATN-161) Blocks Breast Cancer Growth and Metastasis in vivo. *Mol. Cancer Ther*, 5:2271-2280 (2006).
Braun, et al., Lack of Effect of Adjuvant Chemotherapy on the Elimination of Single Dormant Tumor Cells in Bone Marrow of High-Risk Breast Cancer Patients, *J. Clinical Oncology*, 18:80-86 (2000).
Braun, et al., Cytokeratin-Positive Cells in the Bone Marrow and Survival of Patients with Stage I, II or III Breast Cancer, *New England Journal of Medicine*, 342: 525-534 (2000).
Wieder, Insurgent Micrometastases: Sleeper Cells and Harboring the Enemy, *Journal of Surgical Oncology*, 89: 207-210 (2005).
Putz, et al., Phenotypic Characteristics of Cell Lines Derived from Disseminated Cancer Cells in Bone Marrow of Patients with Solid Epithelial Tumors: Establishment of Working Models for Human Micrometastases, *Cancer Research*, 59:241-248 (1999).
Howlett et al., Cellular growth and survival are mediated by β1 integrins in normal human breast epithelium but not in breast carcinoma, Journal of Cell Science, 108:1945-1957 (1995).
Jones et al., Alteration of Stromal Protein and Integrin Expression in Breast—A Marker of Premaligant Change?, Journal of Pathology, 167:399-406 (1992).
Mechtersheimer et al., Expression β1 integrins in non-neoplastic mammary epithelium, fibroadenoma and carcinoma of the breast, Virchows Archiv A Pathol Anat, 422:203-210 (1993).

(Continued)

*Primary Examiner*—Larry R. Helms
*Assistant Examiner*—Meera Natarajan
(74) *Attorney, Agent, or Firm*—Klauber & Jackson LLC

(57) ABSTRACT

The present invention provides for identification of agents that induce growth arrest and survival of cancer cells, which remain dormant in bone marrow, thus preventing their eradication through use of standard chemotherapy or radiation therapy. Basic fibroblast growth factor (FGF-2), a mammary differentiation factor abundant in the bone marrow stroma, induces growth arrest of relatively differentiated breast cancer cells and restricts their survival to fibronectin by upregulating integrin α5β 1. Most of the FGF-2-arrested cells fail to establish optimal ligation to fibronectin and undergo cell death. Cells that do attach to fibronectin, another major constituent of the bone marrow microenvironment, stay alive and growth-arrested for many weeks. Using function-blocking antibodies and peptides, a specific contribution of α5β1-fibronectin interaction in maintaining survival of growth-arrested cells was demonstrated. The present invention thus allows for methods, agents and pharmaceutical compositions that can be used to potentiate the activity of chemotherapy or radiation therapy.

8 Claims, 18 Drawing Sheets

OTHER PUBLICATIONS

Aoudjit, F. et al, (2001) Integrin Signaling Inhibits Paclitaxel-Induced Apoptosis in Breast Cancer Cells, Oncogene, vol. 20, 4995-5004.

Lotan, R., (1979) Different Susceptibilities of Human Melanoma and Breast Carcinoma Cell Lines to Retinoic Acid-Induced Growth Inhibition, Cancer Res. vol. 39, 1014-1019.

Fraker, L.D. et al (1984) Growth Inhibition by Retinol of a Human Breast Carcinoma Cell Line in Vitro and in Athymic Mice, Cancer Res. vol. 44, 5757-5763.

\* cited by examiner

A.

B.

C.

A.

B.

A.
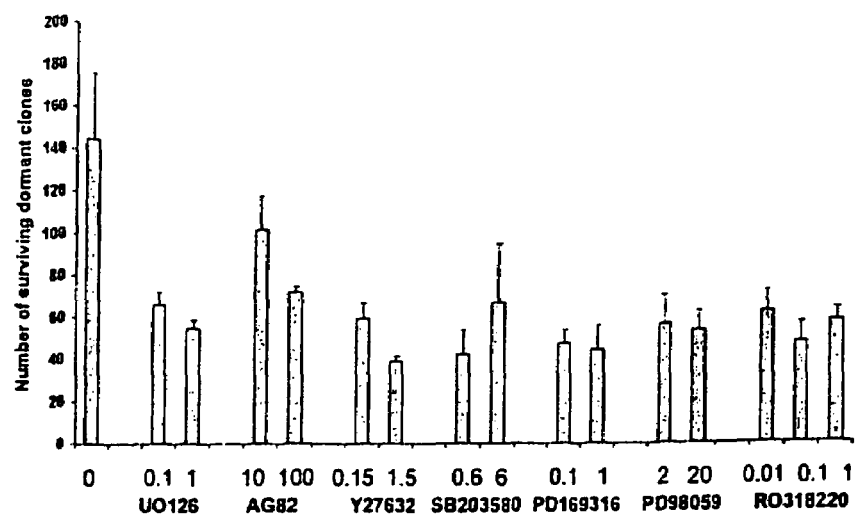
B.
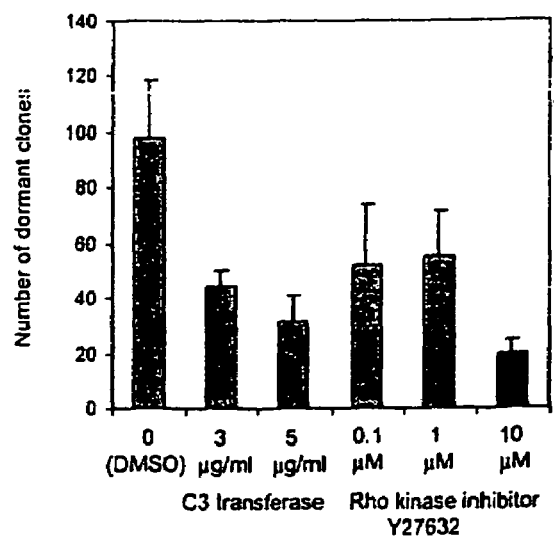
Figure 17 A&B

ALPHA 5 BETA 1 AND ITS ABILITY TO REGULATE THE CELL SURVIVAL PATHWAY

CROSS-REFERENCE TO RELATED APPLICATIONS

The present application claims the priority of copending provisional U.S. Ser. No. 60/396,482, filed on Jul. 16, 2002, the disclosure of which is hereby incorporated by reference herein in its entirety. Applicants claim the benefits of this application under 35 U.S.C. §119(e).

GOVERNMENT RIGHTS CLAUSE

The research leading to the present invention was supported, at least in part, by U.S. Army Grant No. DAMD17-01-C-0343. Accordingly, the Government may have certain rights in the invention.

FIELD OF THE INVENTION

The invention relates generally to the field of oncology, cancer metastasis and cellular proliferation. In particular, this invention relates to the identification of methods of interrupting certain elements of the cell survival pathway, which then allows for enhanced efficacy of traditional modes of cancer therapy, including chemotherapy and radiation therapy. More particularly, the invention relates to the use of kinase or transcription inhibitors for pre-treatment to sensitize for, or concurrent treatment to potentiate chemotherapy or radiation therapy for treatment of cancers or hyperproliferative disorders. The invention also provides for the use of kinase or transcription inhibitors to downregulate expression of the alpha 5 beta 1 integrin and/or phosphorylation of Akt to treat cancer or hyperproliferative disorders. Blocking antibodies specific for the alpha 5 beta 1 integrin are also envisioned for use in either pretreatment to sensitize for, or to be used concurrently with chemotherapy or radiation therapy for treatment of cancer or hyperproliferative disorders. Methods of treatment of cancer or hyperproliferative disorders using fibronectin binding blocking peptides to sensitize for or potentiate chemotherapy or radiation therapy are also envisioned by the present invention. Furthermore, the invention relates to methods of use of retinoids to decrease the expression or phosphorylation of Akt and treatment of cancer or hyperproliferative disorders. The instant invention also provides for pharmaceutical compositions comprising, and methods of using the agents of the present invention for treatment of cancer or hyperprolifeartive disorders. Screening methods for identification of novel agents for use in treating cancer or hyperproliferative disorders in accordance with the present invention is also disclosed.

BACKGROUND OF THE INVENTION

Breast cancer cells metastasize to the bone marrow early in the course of the disease (Braun, S., et al. (2000) *The New England J. Med.* 342, 525-533). Most metastatic cells die upon reaching the marrow microenvironment, but some well-differentiated cells that survive can remain dormant, or growth arrested without loss of viability, for years (Boyce, B. F., et al. (1999) *Endocrine-Related Cancer* 6, 333-347; Chang, J., et al. (1999) *J. Clinical Oncology* 17, 3058-3063). They remain protected from death and, in fact, survive multiple rounds of adjuvant chemotherapy administered specifically to eradicate them (Braun, S., et al. (2000) *J. Clin. Onc.* 18, 80-86). The factors and the mechanisms that induce dormancy, that is, growth arrest coupled with long-term survival, of occult breast cancer cells in bone marrow microenvironment and which protect the cells from chemotherapy remain largely unknown. However, a variety of growth factors and ligands of cellular integrins in the marrow microenvironment may influence the fate of the metastatic cell. These factors have well-established effects on cell behavior, including protection of hematopoietic stem cells (Ploemacher, R. E. (1997) *Baillieres Clinical Haematology* 10, 429-444; Knaan-Shanzer, S., et al., (1999) *Experimental Hematology* 27, 1440-1450).

Bone marrow stroma is a rich source of growth factors such as epidermal growth factor (EGF), insulin-like growth factor (IGF-1) and basic fibroblast growth factor (FGF-2). FGF-2, a factor implicated in mammary ductal differentiation, induces growth arrest in a variety of relatively differentiated breast cancer cells.

However, there is a further need for identification of the factors responsible for growth arrest and long-term survival of occult cancer cells, as well as a better understanding of the mechanisms involved. Upon identification of the factors involved, novel therapeutics may be developed which could be used as stand-alone therapies or may be used as adjunct therapy with other standard forms of therapy to treat cancer or hyperproliferative disorders, such as chemotherapy or radiation therapy. It is with respect to this unmet need that the current invention is directed.

Other advantages of the present invention will become apparent from the ensuing detailed description taken in conjunction with the following illustrative drawings.

SUMMARY OF THE INVENTION

It is known that malignant cells from breast cancer micrometastases as well as other hyperproliferative disorders in bone marrow remain dormant without loss of viability for prolonged periods of time. It is in this growth arrested estate that the cells are resistant to standard forms of therapy including chemotherapy or radiation therapy. The factors that induce this dormancy are unknown at this time. It is thus an object of the present invention to identify the factors responsible for this dormancy, and to utilize these factors for identification, use of, and screening for new therapeutic regimens for treatment of cancer and other hyperproliferative disorders.

A first aspect of the invention provides for the identification and use of kinase or transcription inhibitors as pretreatment or concurrent treatment, to sensitize for or potentiate chemotherapy in the treatment of cancer or hyperproliferative disorders. In a preferred embodiment, the agents identified by the present invention are inhibitors of MAP kinase, Rho kinase, PI3 kinase and/or PKC kinase.

In another preferred embodiment, the kinase or transcription inhibitors are used to treat metastatic cancers and/or hyperproliferative disorders. In another preferred embodiment, the kinase or transcription inhibitors are used to treat breast cancer. In yet another preferred embodiment, the kinase or transcription inhibitors are used to treat metastatic breast cancer.

In a second aspect of the invention, the kinase or transcription inhibitors are used to downregulate expression of the alpha 5 beta 1 integrins.

In a third aspect of the invention, the kinase or transcription inhibitor decreases expression and/or phosphorylation of Akt and is utilized for treatment of cancer or hyperproliferative disorders.

A fourth aspect of the invention provides for the use of antibodies to integrin alpha 5 beta 1 as pretreatment or concurrent treatment to sensitize for, or potentiate chemotherapy or radiation therapy in the treatment of cancer or hyperproliferative disorders.

In a preferred embodiment, the antibodies are used to treat metastatic cancers or other hyperproliferative disorders. In another preferred embodiment, the antibodies are used to treat breast cancer. In yet another preferred embodiment, the antibodies are used to treat metastatic breast cancer. The antibodies may be polyclonal or monoclonal. They may be single chain antibodies. They may be chimeric antibodies. They may be Fab fragments or soluble components thereof. They may be human or humanized. They may be produced in other animals, including but not limited to horses, goats, sheep, mice, rats, rabbits and guinea pigs.

A fifth aspect of the invention provides for the use of fibronectin binding blocking peptides as pretreatment or concurrent treatment, to sensitize for or potentiate chemotherapy or radiation therapy in the treatment of cancer or hyperproliferative disorders.

In a preferred embodiment, the fibronectin binding blocking peptides are used to treat breast cancer. In yet another preferred embodiment, the fibronectin binding blocking peptides are used to treat metastatic breast cancer.

A sixth aspect of the invention provides for the use of retinoids to decrease expression or phosphorylation of Akt and treatment of cancers or hyperproliferative disorders.

In a preferred embodiment, the retinoids are used to treat metastatic cancers or other hyperproliferative disorders. In another preferred embodiment, the retinoids are used to treat breast cancer. In yet another preferred embodiment, the retinoids are used to treat metastatic breast cancer.

A seventh aspect of the invention provides for a method of inhibiting cellular proliferation in a mammal suffering from a disease or a disorder characterized by cellular proliferation, the method comprising administering an effective amount of a kinase or transcription inhibitor prior to, or concurrent with chemotherapy or radiation therapy. In a preferred embodiment, the kinase inhibitor is selected from the group consisting of LY294002, UO 126, AG82, Y27632, SB203580, PD169316, PD98059, RO318220, or C3 transferase inhibitor.

In another preferred embodiment, the disease or disorder characterized by cellular proliferation is cancer or a hyperproliferative disorder. In another preferred embodiment, the cancer is a metastatic cancer. In another preferred embodiment, the cancer is breast cancer. In yet another preferred embodiment, the breast cancer has metastasized.

In a yet further preferred embodiment, the kinase or transcription inhibitor downregulates expression of the alpha 5 beta 1 integrins or phosphorylation of Akt to sensitize for or potentiate chemotherapy or radiation therapy in mammals in need thereof.

An eighth aspect of the invention provides for a method for disrupting survival signaling from the microenvironment in cancer cells, wherein said disrupting results in sensitizing cells to chemotherapy, biological therapies or radiation therapy of cancer micrometastases and hyperproliferative disorders in a mammal. In a preferred embodiment, the integrin is alpha 5 beta 1 and the extracellular matrix protein is fibronectin. In another preferred embodiment, the cancer is breast cancer or prostate cancer. In yet another preferred embodiment, the method comprises administration of an antibody specific for an integrin or a blocking peptide or modified peptide that disrupts interaction of the integrin with the extracellular matrix. In a yet further preferred embodiment, the method comprising administration of all trans retinoic acid or a retinoic acid derivative. A yet further embodiment comprises decreasing expression of cell surface integrins with a transcription inhibitor, or blocking survival signaling initiated by ligation of integrins by microenvironment proteins. A most preferred embodiment provides for treatment with an inhibitor of a kinase, said kinase selected from the group consisting of MAP kinase, Rho kinase, PI3 kinase and PKC kinase. The most preferred inhibitors are selected from the group consisting of LY294002, UO 126, AG82, Y27632, SB203580, PD169316, PD98059, RO318220, and a 3 transferase inhibitor.

A ninth aspect of the invention provides for a method for treating hyperproliferative disorders in a mammal, comprising administration of an agent capable of blocking the binding of integrins with the extracellular matrix. In a preferred embodiment the integrins comprises alpha 5 beta 1 and the matrix is fibronectin.

A tenth aspect of the invention provides for the use of an agent for the preparation of a composition for treatment of hyperproliferative disorders, said agent capable of downregulation of the expression of the alpha 5 beta 1 integrins and its binding to the extracellular matrix.

An eleventh aspect of the invention provides for pharmaceutical compositions comprising the kinase or transcription inhibitor and a pharmaceutically acceptable carrier, or an antibody, blocking peptide or modified peptide and a pharmaceutically acceptable career.

Other objects and advantages will become apparent from a review of the ensuing detailed description and attendant claims. All references cited in the present application are incorporated herein in their entirety.

MCF-7 cells were incubated at a concentration of 1000 cells/well on 24 well plates coated with A. collagen I or B. fibronectin or laminin I for variable periods from 3 to 9 days, stained with crystal violet and photographed. A. Colony cultures in collagen I-coated dishes demonstrating increased colony formation with time in the two control rows and with 10 ng/ml EGF-treatment and almost complete abolition of colony formation by FGF-2 10 ng/ml. Experiments were done at least twice with similar results. B. Similar cellular obliteration was observed on laminin I-coated plates, but incubation on fibronectin yielded survival of a small number of nonproliferating cells. Shown are typical 5 day colonies in control wells and impaired colony formation in wells containing FGF-2 10 ng/ml.

Figure 3:
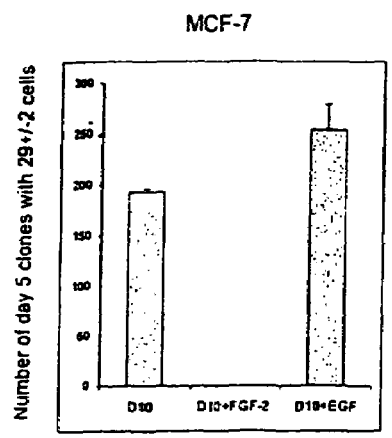
Figure 3:
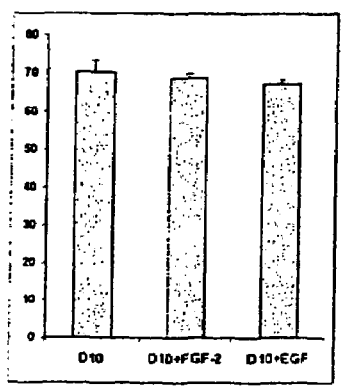
Figure 3:
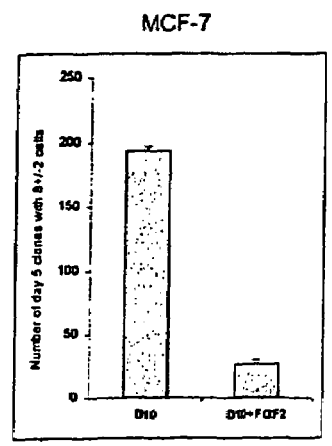
Figure 3:
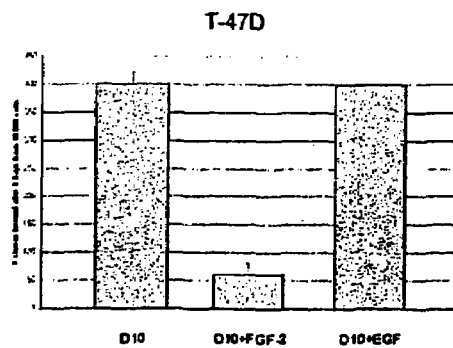

FIG. 3. FGF-2 inhibits the clonogenicity of MCF-7 cells but has no effect on MDA-MB231 cell One thousand MCF-7 or MDA MB-231 cells per well were incubated in 24 well tissue culture plates with and without the presence of 10 ng/ml basic fibroblast growth factor (FGF-2) or epidermal growth factor (EFG). Plates were stained with crystal violet after a 5 day incubation and clones consisting of A. 29±2 cells and B. 8±2 cells were counted. C. Ten thousand T-47D cells per well were incubated in 24 well tissue culture plates coated with fibronectin with and without the presence of 10 ng/ml basic fibroblast growth factor (FGF-2) or epidermal growth factor (EFG). Plates were stained with crystal violet after 3 days and clones consisting of 8 or more cells were counted.

Figure 4:
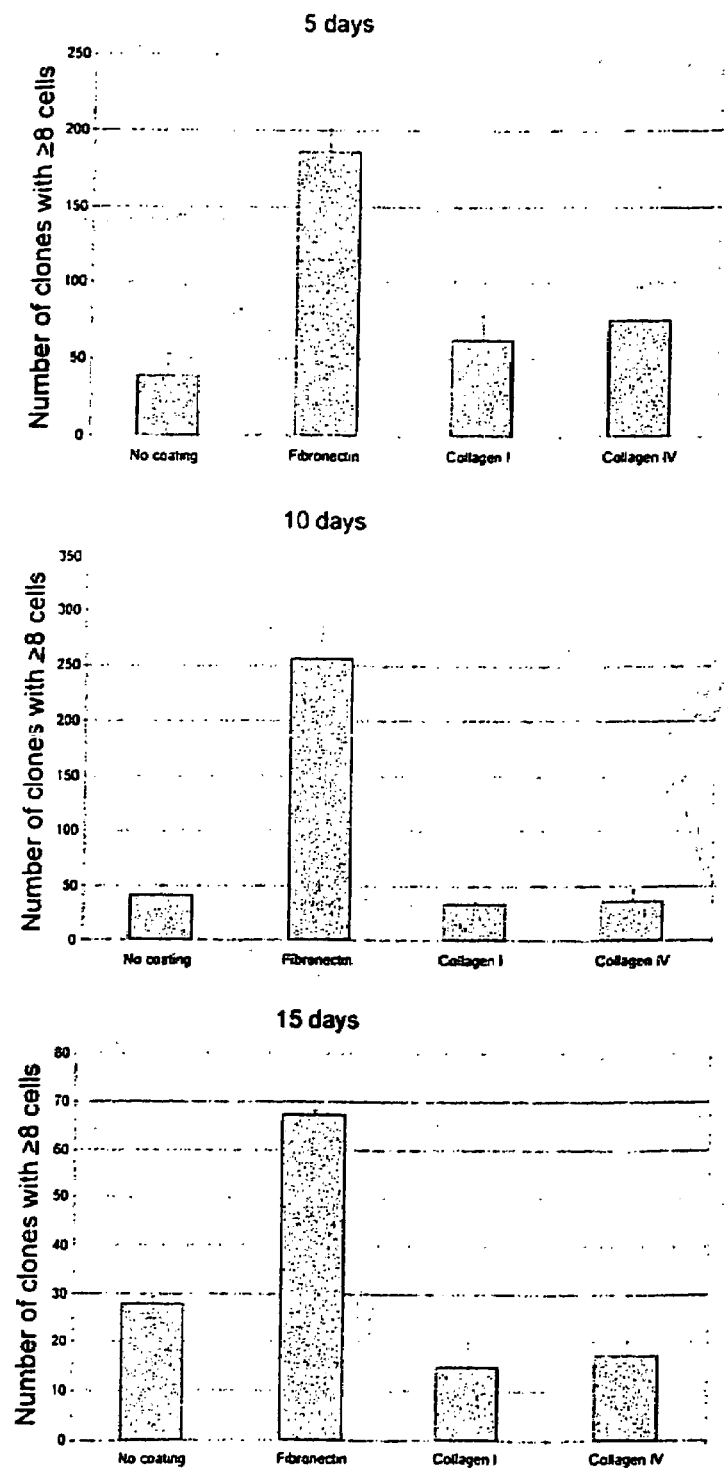

FIG. 4. Cloning efficiency of MCF-7 cells in the presence of FGF-2

Five thousand MCF-7 cells were incubated per well in duplicate on 6 well tissue culture dishes with various substrata with FGF-2 10 ng/ml. Colonies of 8 cells or greater were counted after staining the plates with crystal violet after 5, 10 and 15 day incubations. Incubation on fibronectin continued to preserve the clonogenicity of these cell lines for up to the 15 days assayed.

Figure 5:
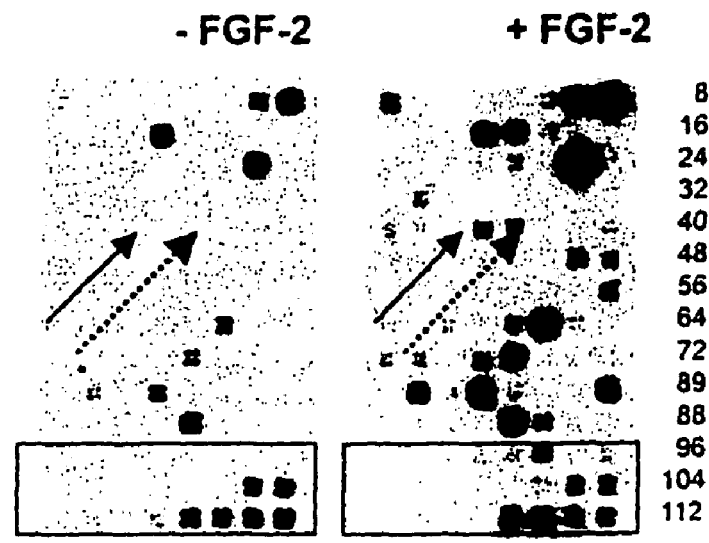
Figure 5:
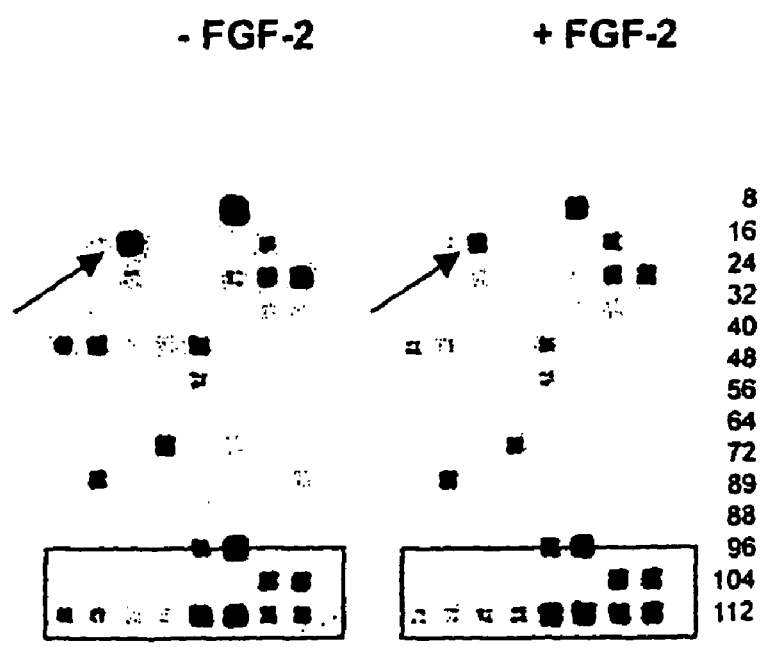

FIG. 5. Nonrad GEArray Q series gene chip microarray analysis of MCF-7 cells incubated with and without FGF-2 for 5 days on tissue culture dishes coated with fibronectin Gene chip microarray analysis of MCF-7 cells incubated for 5 days on tissue culture dishes coated with fibronectin 20 µg with and without the presence of FGF-2 10 ng/ml. Approximately one third as many cells remained in the FGF-2-treated population as in the control cells. A. Nonrad GEArray Q series Human Extracellular Matrix and Adhesion Protein chip (Super Array, Bethesda, Md.). Arrows point to integrin α5 (solid line) and α6 (dotted line) mRNA's that are elevated in the surviving population. Boxes are drawn around the control gene cDNAs on the two chips consisting of GAPDH, Cyclophyllin A, ribosomal L23 and β actin as positive controls and PUC18 plasmid DNA and blanks as negative controls. B. Nonrad GEArray Q series Human Pathway Finder chip (Super Array, Bethesda, Md.). Arrow points to the p16$^{INK4}$ gene whose expression is downregulated by FGF-2 treatment on fibronectin. Numbers on right of chips indicate the numbering of the rightmost member cDNA of each row.

Changes in gene expression due to FGF-2 treatment on a fibronectin-coated plate for five days were observed in the following genes on the two chips noted in Table 1 and Table 2.

Figure 6:
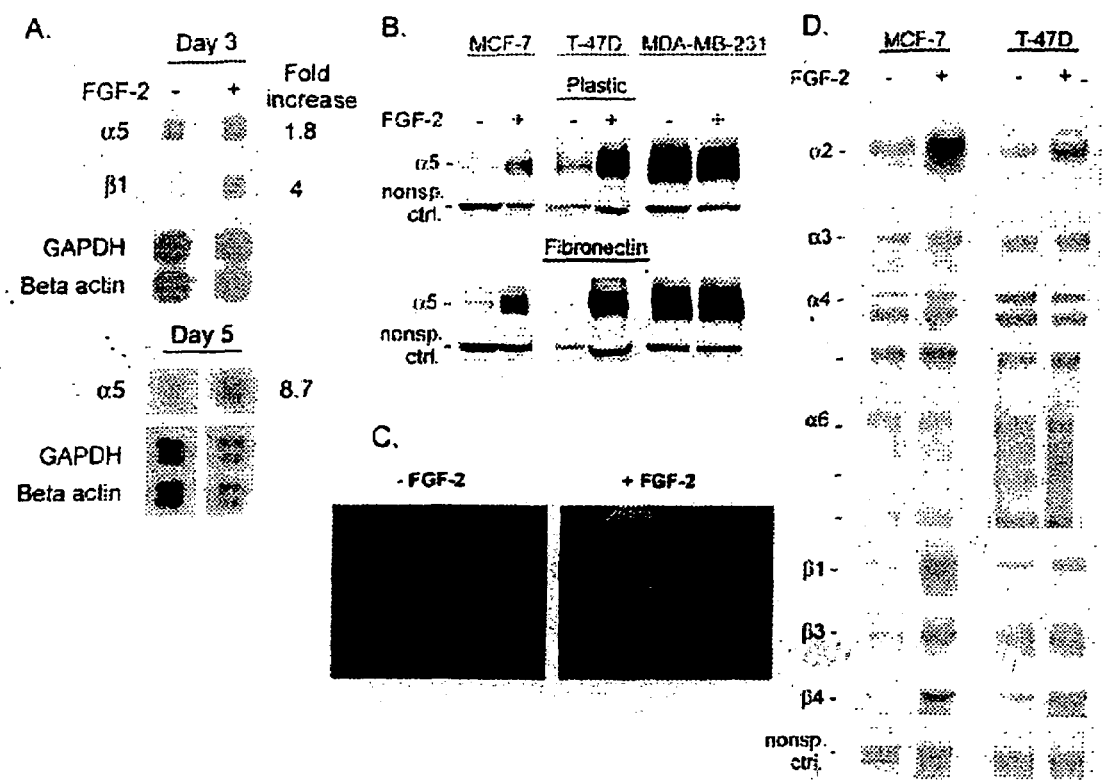

FIG. 6. FGF-2 regulates expression of integrins.

A. Gene chip analysis of integrin α5 and β1 mRNA expression in MCF-7 cells incubated±FGF-2 for 3 or 5 days on fibronectin-coated plates. Densitometer quantitations normalized against GAPDH and actin mRNA standards are shown. B. Western blots of integrin α5 from cells incubated±FGF-2 for 3 days on tissue culture- or fibronectin-coated dishes. C. Indirect immunofluorescence of integrin α5 in T-47D cells on cover slips±FGF-2 10 ng/ml for 24 hours. D. Western blots of integrins α2, α3, α4, α6, β1, β3 and β4 in MCF-7 and T-47D cells incubated±FGF-2 for 3 days. Non-specific bands were as loading controls.

Figure 7:
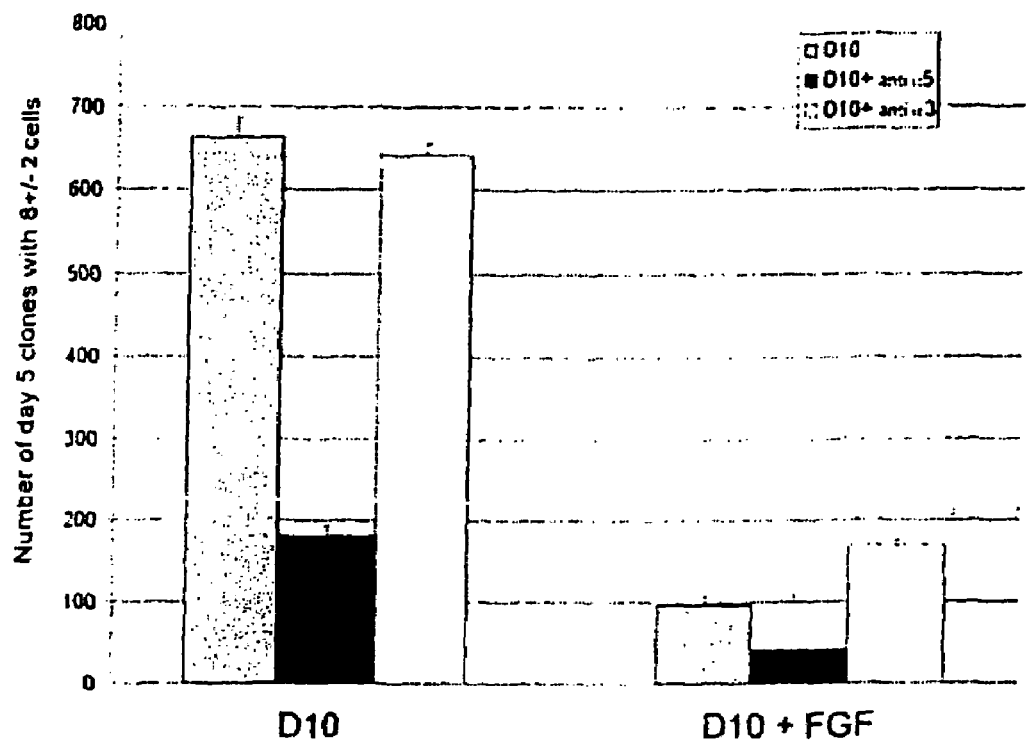

FIG. 7. Integrin α5-dependent clonogenic survival of MCF-7 cells on fibronectin

Five thousand MCF-7 cells were incubated per well in quadruplicate on 5-well tissue culture dishes with and without 10 ng/ml FGF-2, in the presence or absence of 2 µg neutralizing mouse monoclonal antibody to integrin α5 or integrin α3 (Chemicon, Inc, Temecula, Calif.). Cells were cultured for 5 days, stained with crystal violet and clones with 8±2 cells were counted.

Figure 8:
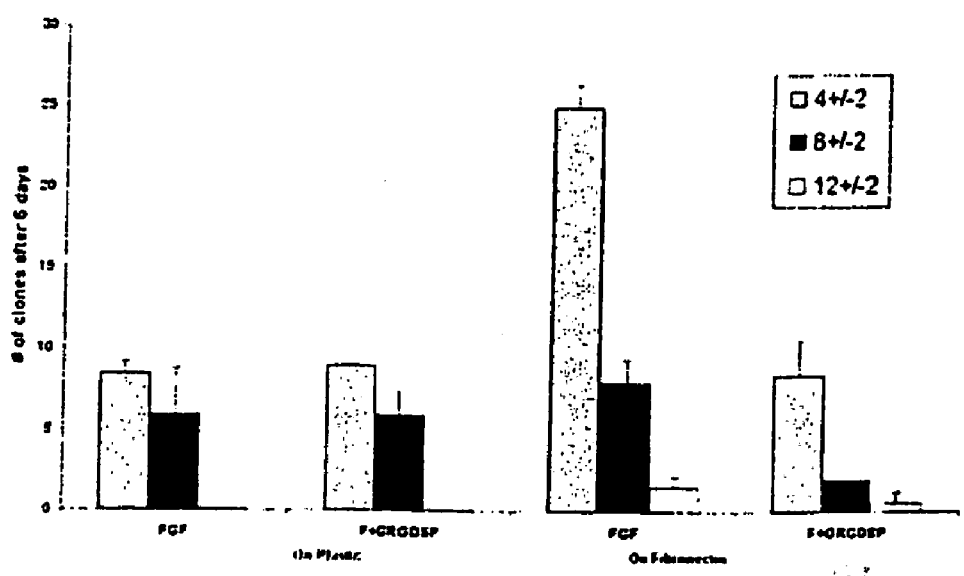

FIG. 8. Fibronectin-specific blocking peptides selectively inhibit clonogenicity on fibronectin.

$10^3$ MCF-7 (and T-47D, not shown) cells were incubated±fibronectin with 10 ng/ml FGF-2. Fibronectin-blocking peptide GRGDSP 1 ng/ml (American Peptide Co., Inc, Sunnyvale, Calif.) was added after 3 days and 4, 8 and 12 cell colonies were counted 6 days later. Blocking peptide only inhibited colonies on fibronectin, and not on plastic.

Figure 9:
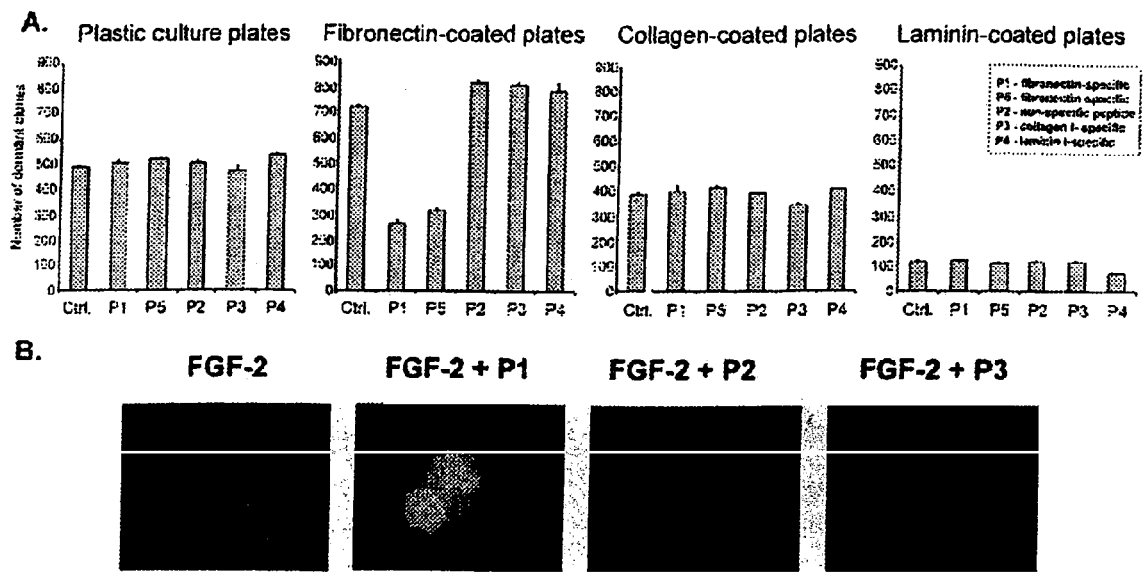

FIG. 9. Ligation of Integrin α5β1 provides specific protection from cell death in well-differentiated breast cancer cells A. MCF-7 cells (and T-47D cells, not shown) were incubated with FGF-2 on variably coated plates. Blocking peptides were added after 3 days. Colonies with ≦10 cells were stained with crystal violet at 6 days and counted. B. T-47D cells were incubated on fibronectin-coated plates with FGF-2 and blocking peptides were added after 3 days. Cells were probed 24 hours later with anti-integrin α5 antibody and Texas Red-tagged secondary antibody and assayed by TUNEL-FTIC.

Figure 10:
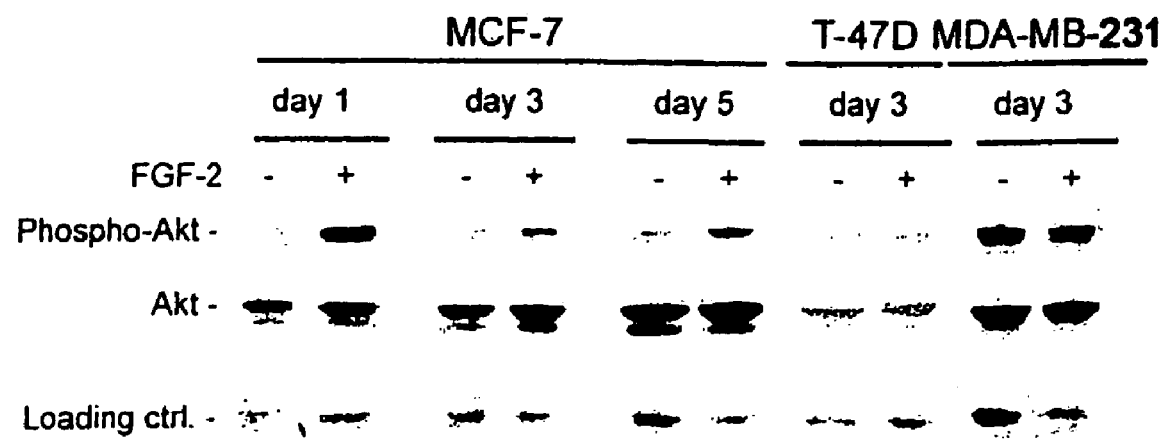

FIG. 10. Induction of sustained Akt phosphorylation by FGF-2 on fibronectin

Western blots of lysates from MCF-7, T-47D and MDA-MB-231 cells incubated on fibronectin-coated plates with FGF-2 for up to 5 days were stained with antibody to phospho-Akt or total Akt. Blots show sustained phosphorylation of Akt by FGF-2 in MCF-7 and T-47D cells but no effect on constitutive Akt phosphorylation in MDA-MB-231 cells. No effect was noted on total Akt levels. Stained membrane was used as a loading control.

Figure 11:
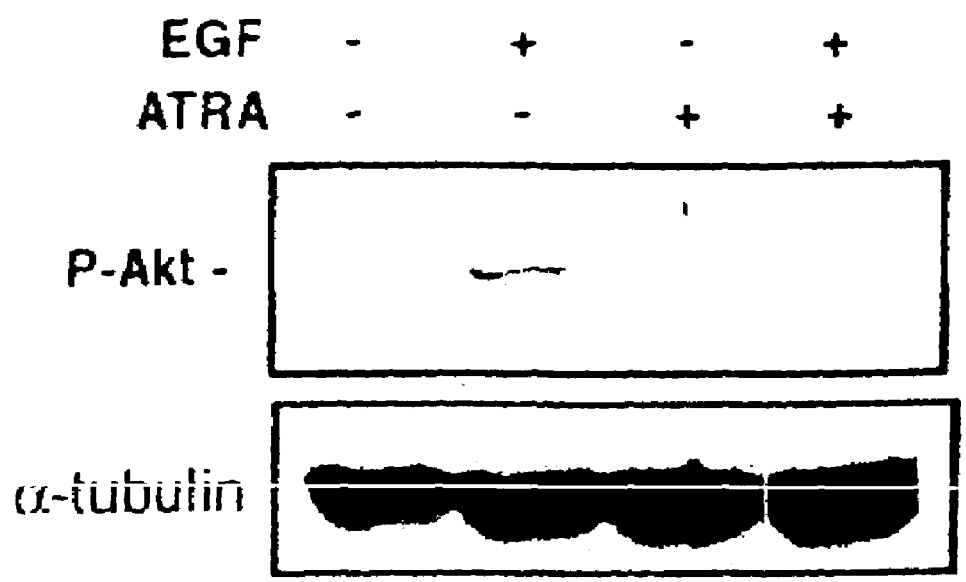

FIG. 11. All-trans retinoic acid dampens EGF-mediated AKT phosphorylation

MCF-7 cells were treated with EGF 100 ng/ml for 10 min followed by ATRA $10^{-7}$ M or control media 2 h later for an additional 24 h. Western blots of lysates were stained with anti-phospho-Akt ab.

Figure 12:
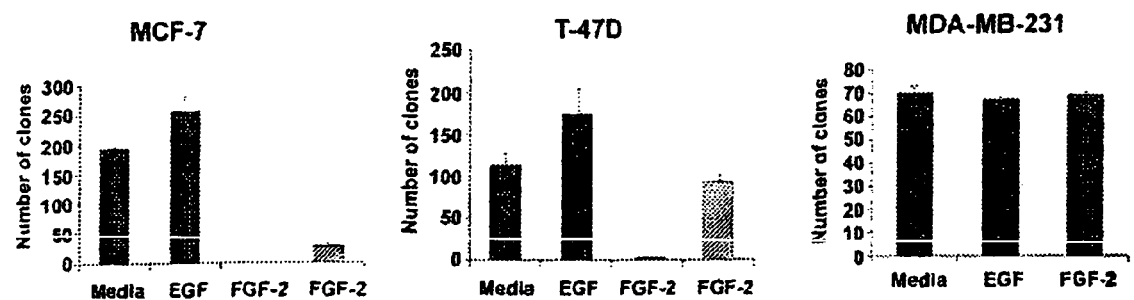

FIG. 12. Effects of EGF and FGF-2 on the clonogenic potential of well and poorly-differentiated breast cancer cells in tissue culture MCF-7 and T-47D (1,000 cells/well) and MDA MB-231 (200 cells per well) were incubated in 24 well plates±10 ng/ml EFG or FGF-2 for 6 days, stained with crystal violet and clones with ≧29 actively growing cells (■) or with ≦10 well spread, growth arrested cells (▨) were counted.

Figure 13A:
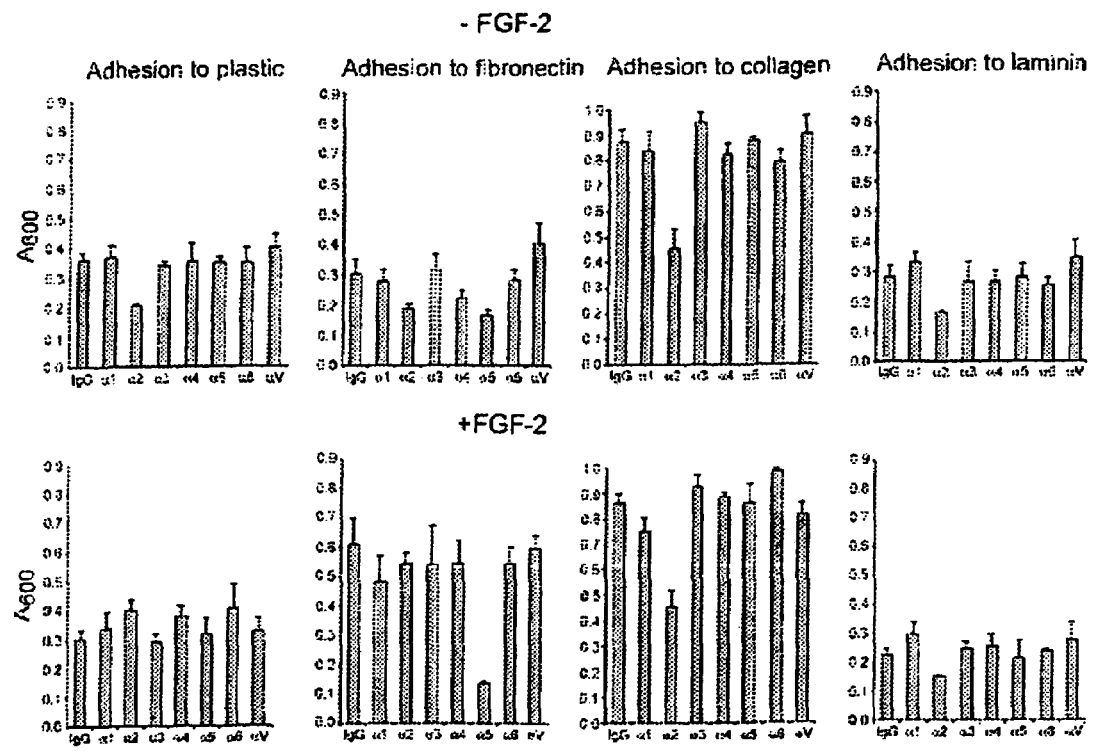
Figure 13B:
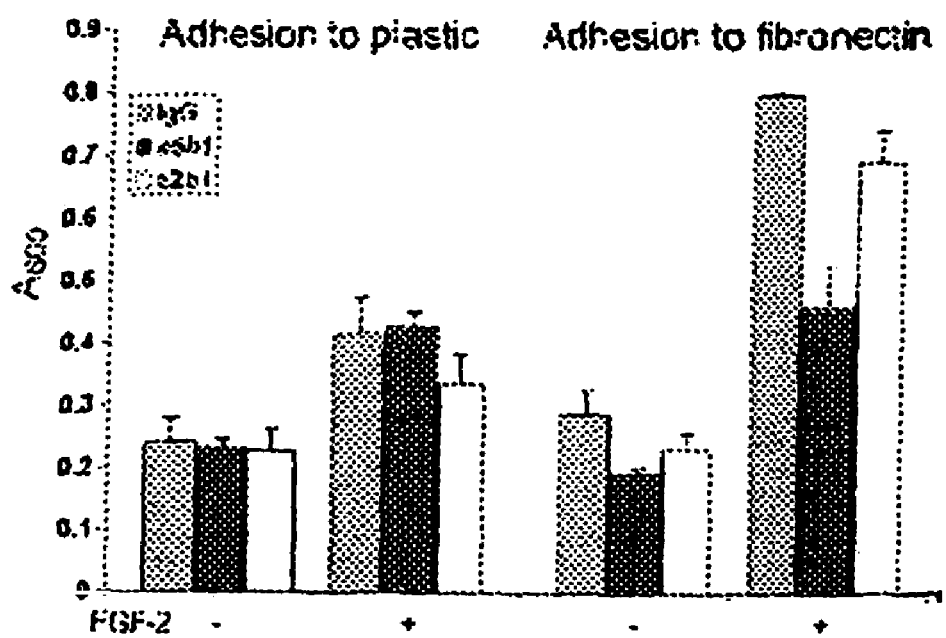

FIG. 13. Adhesion of breast cancer cells to stromal proteins

Both MCF-7 and T-47D cells were cultured±FGF-2 on tissue culture (A) or on fibronectin-coated plates (B), detached with Cell Dissociation Solution, washed with PBS and counted. Cells were incubated with 2 µg/ml blocking monoclonal antibodies to the integrins or mouse IgG for 30 minutes at 37° C. and 50,000 cells were incubated in 24 well variably-coated tissue culture plates for 45 minutes at 37° C. Attached cells were stained with crystal violet and the $A_{600}$ of the extracted dye was measured, as described. Results were similar for both cells. Shown are data for T-47D (A) and MCF-7 cells (B). Antibody to integrin α blocked adhesion to fibronectin in FGF-2 treated cells by 75% but only inhibited untreated cell adhesion by a third. Blocking antibody to α2 decreased adhesion to collagen and laminin in both FGF-2 treated and untreated cells equally. While adhesion to collagen surpassed adhesion to fibronectin, it did not support dormant clone survival. These adhesion controls demonstrated that the data are consistent with a specific survival effect derived from ligation to fibronectin in dormant cells and not merely an effect due to nonspecific adhesion.

Figure 14:
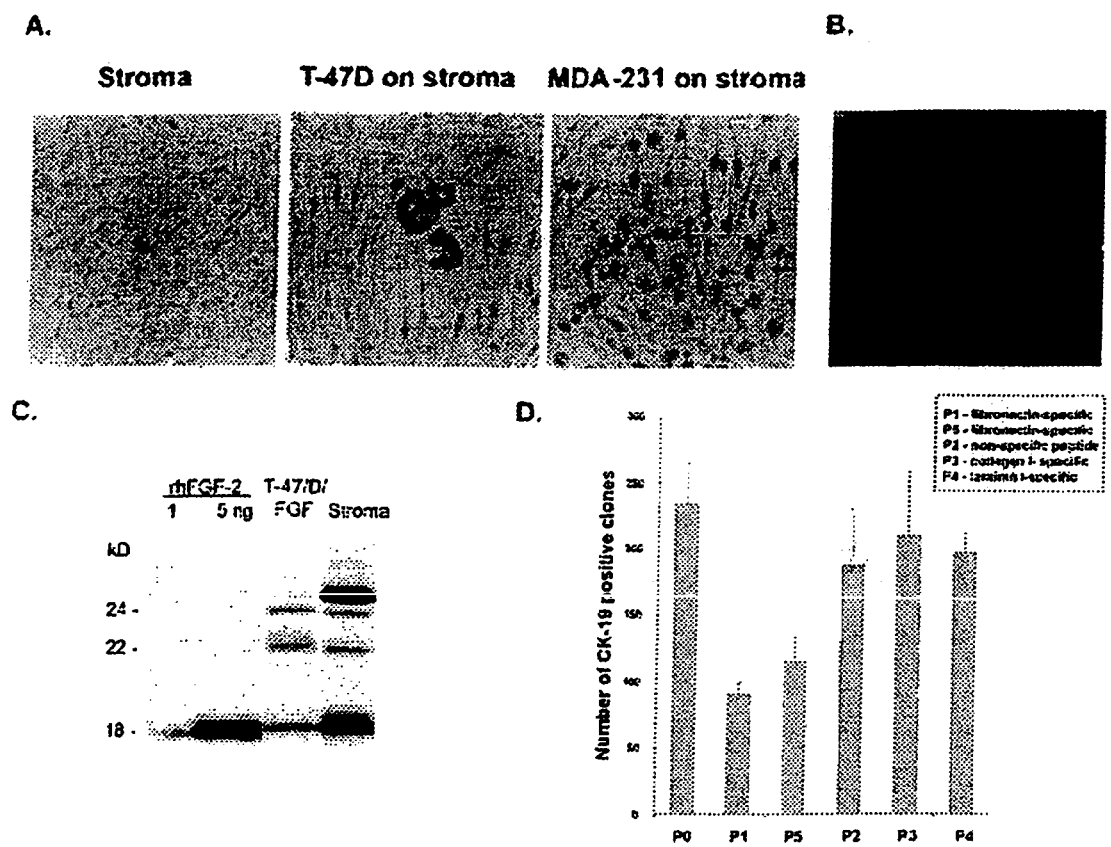

FIG. 14. Stroma restricts growth of well-differentiated T-47D breast cancer cells.

A. Confluent stromal cultures in 24 well plates seeded with 500 T-47D or MDA-MB-231 cells/well were cultured for 6 days. B. Cytokeratin 19 immunofluorescence (red) staining of MCF-7 cells on stromal co-culture (blue background) demonstrating a primarily single cell status of MCF-7 cells after 6 days. C. Western blots of stromal cell lysates (100 μg) with recombinant FGF-2 and lysates from T-47D cells transfected with a vector expressing 18, 22, 22.5 and 24 kD FGF-2 isoforms. D. MCF-7 cells were seeded on stromal monolayers on 24 well plates (1,000 cells/well). Blocking peptides were added after 3 days. At 6 days, plates were stained with anti-cytokeratin 19 antibody and horseradish peroxidase-tagged secondary antibody, developed and colonies of ≦10 cells counted.

Figure 15:
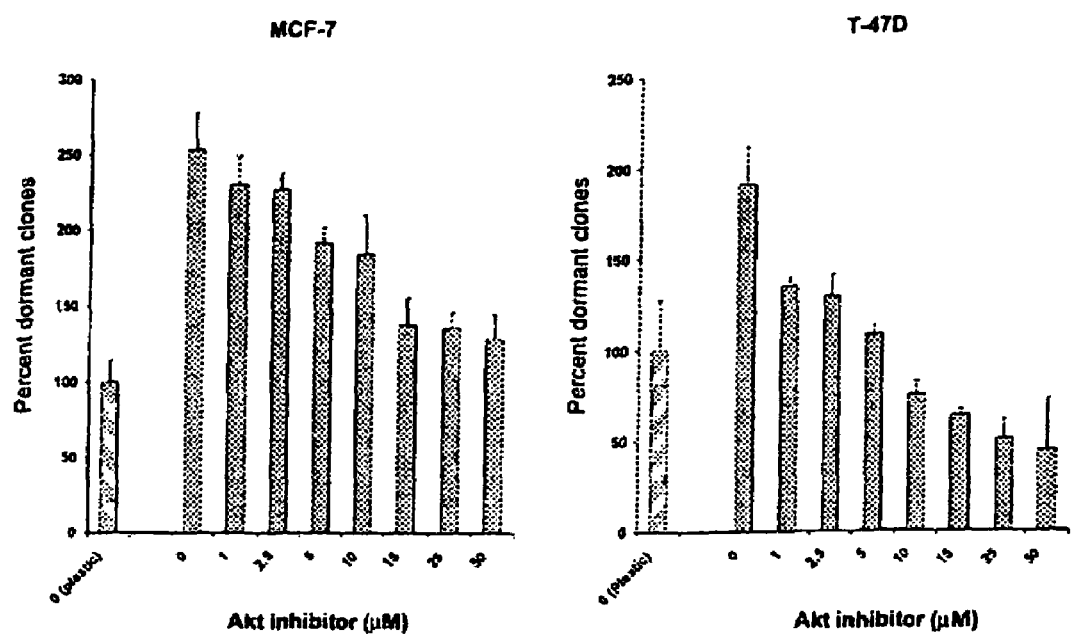

FIG. 15. Akt-inhibitor reduces fibronectin-promoted survival of dormant breast cancer cell clones.

MCF-7 and T-47D cells were incubated with FGF-2 on fibronectin for three days, media was changes and supplemented with variable concentrations of inhibitor and fresh FGF-2 and incubated for an additional three days. Colonies≦10 cells were counted after crystal violet staining. Data is plotted as percent change from colony numbers on tissue culture coated plastic dishes.

Figure 16:
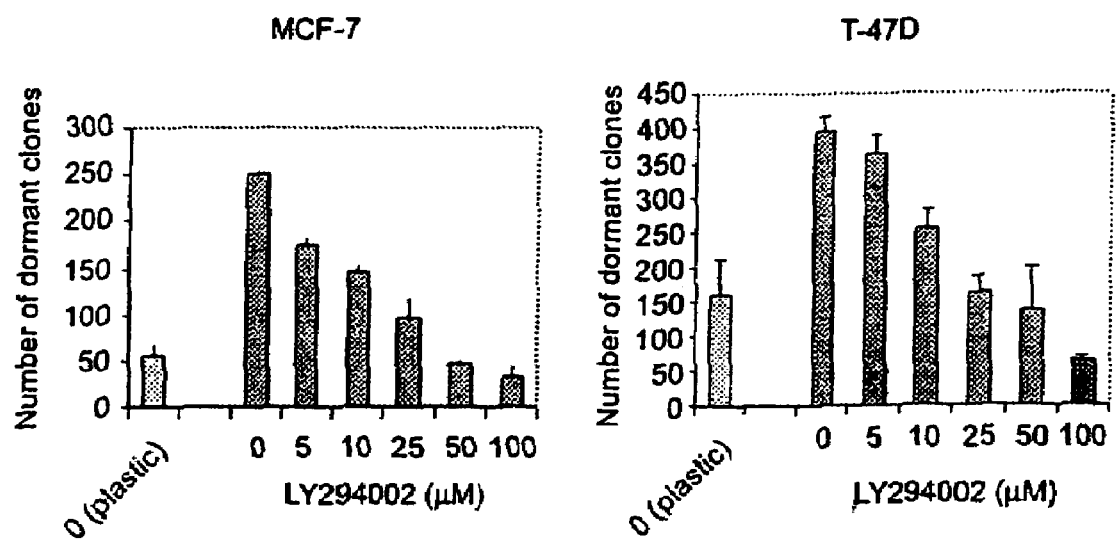

FIG. 16. The phosphatidyl inositol 3-kinase (PI3 kinase) inhibitor LY294002 reduces fibronectin-promoted survival of dormant breast cancer cell clones.

MCF-7 and T-47D cells were incubated with FGF-2 on fibronectin for three days, media was changed and supplemented with variable concentrations of inhibitor and fresh FGF-2 and incubated for an additional three days. Colonies≦10 cells were counted after crystal violet staining.

FIG. 17. Inhibition of dormant clone survival by kinase inhibitors.

A. MCF-7 cells (and T-47D cells, not shown) and B. T-47D cells were incubated with FGF-2 on fibronectin for three days, media was changed and supplemented with variable concentrations of a variety of kinase inhibitors and a small GTPase inhibitor and fresh FGF-2, and incubated for an additional three days. Control cells were incubated in 10 μM DMSO as control for the solvent used with the inhibitors. Colonies≦10 cells were counted after crystal violet staining. Data are plotted as percent change from colony numbers on tissue culture coated plastic dishes demonstrating significant inhibition of dormant clones by abrogating a number of signaling pathways. C. The inhibitors used were:

| Inhibitor | Target | ED50 |
| --- | --- | --- |
| UO 126 | MEK 1 | 72 nM |
|  | MEK 2 | 58 nM |
| AG82 | FAK | 7 μM |
| Y27632 | Rho kinase | 140 nM |
| SB203580 | p38 | 600 nM |
| PD169316 | p38 | 89 nM |
| PD98059 | MEK | 2 μM |
| RO318220 | Protein kinase C | 10 nM |
|  | Protein kinase A | 900 nM |
| C3 transferase inhibitor | RhoA | 2–5 μg/ml |

DETAILED DESCRIPTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

DEFINITIONS

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

The term "antibody" as used herein includes intact molecules as well as fragments thereof such as Fab and F(ab')$_2$, which are capable of binding the epitopic determinant. Antibodies that bind the proteins of the present invention can be prepared using intact polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be a single chain antibody. The antibody may be prepared in mice, rats, rabbits, goats, sheep, swine, dogs, cats, or horses.

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (eg. to inhibit cellular proliferation and to sensitize for, or potentiate chemotherapy or radiation therapy for treatment of mammals having cancer or hyperproliferative disorders), but need not necessarily comprise a sequence that is similar or identical to the sequence of the preferred embodiment, or possess a structure that is similar or identical to the agents of the present invention. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, atea amino acid residues, at least 90 amino acid residues, at least 100 amino acid residues, at least 125 amino acid residues, or at least 150 amino acid residues) of the AAPl; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quaternary structure as that of the preferred embodiment. The structure of a polypeptide can determined by methods known to those skilled in the art, including but not limited to, X-ray crystallography, nuclear magnetic resonance, and crystallographic electron microscopy.

"Derivative" refers to either a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide. It may also refer to chemically synthesized organic molecules that are functionally equivalent to the active parent compound, but may be structurally different. It may also refer to chemically similar compounds which have been chemically altered to increase bioavailability, absorption, or to decrease toxicity.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

A "therapeutically effective amount" is an amount sufficient to decrease or prevent the symptoms associated with the cancer or hyperproliferative disorders or other related conditions contemplated for therapy with the compositions of the present invention.

"Treatment" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Combination therapy" refers to the use of the agents of the present invention with other active agents or treatment modalities, in the manner of the present invention for treatment of cancers or hyperproliferative disorders. These other agents or treatments may include drugs such as other anti-cancer drugs such as those that are standardly used to treat various cancers, radiation therapy, anti-viral drugs, corticosteroids, non-steroidal anti-inflammatory compounds, other agents useful in treating or alleviating pain, growth factors, cytokines, or colony stimulating factors. The combined use of the agents of the present invention with these other therapies or treatment modalities may be concurrent, or the two treatments may be divided up such that the agent of the present invention may be given prior to or after the other therapy or treatment modality.

"Local administration" means direct administration by a non-systemic route at or in the vicinity of the site of an affliction, disorder, or perceived pain.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of treatments necessary to achieve the desired effect in terms of inhibiting cellular proliferation and decreasing the tumor burden or metastatic potential of a cancer or hyperproliferative disorder.

The term "clonogenic potential" refers to the ability of single cells to divide and grow into a cluster of cells. This is a characteristic of metastatic cancer cells in the body. In the lab, it is a reflection of many factors, including viability, health of the cell, injury, and ability to divide on the support provided in the tissue culture dish or in suspension "EGF" is epidermal growth factor; a protein that binds to cell surface receptors and initiates signals that tell the cell to divide, crawl and survive.

"IGF" is insulin-like growth factor; a protein that binds to the insulin-like growth factor receptor that initiates signals that tell the cell to do perform a variety of function from cell division survival, depending on the cell type.

"FGF-2" is fibroblast growth factor 2, basic fibroblast growth factor; a protein that binds to cell surface receptors that initiates a variety of signals that tell different cells to perform different functions. In breast cancer, it can act as a differentiation factor, inhibiting growth and motility.

The term "hyperproliferative disorders" refers to diseases that result from the abnormal growth of cells. These can include cancers, pre-malignant states as well as inflammatory states such as rheumatoid arthritis or conditions such as psoriasis.

"Integrins" are intrinsic cell surface proteins. They mediate cell adhesion by binding with components of the extra cellular matrix, such as fibronectin. This adhesion process is closely tied to the cells ability to survive and reproduce. Many different integrins have been discovered and most have similar structural features eg. they are heterodimeric transmembrane proteins and contain an alpha subunit and a beta subunit. The major fibronectin receptor on most cells is the alpha 5, beta 1 integrin, also referred to in the present application as α5β1. This integrin interacts with the RGD site of the fibronectin molecule.

A kinase is a protein that acts as an enzyme to transfer a phosphate group onto another protein. A "kinase inhibitor" blocks the action of such a protein A "transcription inhibitor" is a chemical or biological that interferes with the synthesis of messenger RNA from a DNA template.

"ATRA" refers to all-trans retinoic acid; a member of a family of compounds called retinoids that act by binding to nuclear receptors called retinoic acid receptors and retinoid X receptors that, when bound to their retinoid ligands, act as transcription factors. ATRA inhibits cell proliferation, induces cell death and potentiates chemotherapy agents in breast cancer cells.

As used herein, the term "modified peptide" may be used to refer to a peptide that is capable of binding to a protein and modulating its activity (e.g., a cell surface receptor). Modified peptides may possess features that, for example, modulate (increase or decrease) binding, alter the half-life of the peptide, decrease renal clearance, or improve absorption.

As used herein, the term "amino acid" and any reference to a specific amino acid is meant to include naturally occurring proteogenic amino acids as well as non-naturally occurring amino acids such as amino acid analogs. One of skill in the art would know that this definition includes, unless otherwise specifically indicated, naturally occurring proteogenic (D) or (L) amino acids, chemically modified amino, acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well-known metabolic pathways.

The choice of including an (L)- or a (D)-amino acid into a peptide of the present invention depends, in part, on the desired characteristics of the peptide. For example, the incorporation of one or more (D)-amino acids can confer increasing stability on the peptide in vitro or in vivo. The incorporation of one or more (D)-amino acids also can increase or decrease the binding activity of the peptide as determined, for example, using the binding assays described herein, or other methods well known in the art. In some cases it is desirable to design a peptide which retains activity for a short period of time, for example, when designing a peptide to administer to a subject. In these cases, the incorporation of one or more. (L)-amino acids in the peptide can allow endogenous peptidases in the subject to digest the peptide in vivo, thereby limiting the subject's exposure to an active peptide.

As used herein, the term "amino acid equivalent" refers to compounds which depart from the structure of the naturally occurring amino acids, but which have substantially the structure of an amino acid, such that they can be substituted within a peptide which retains is biological activity. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents.

As used herein, the term "peptide" is used in its broadest sense to refer to compounds containing amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups.

It is to be understood that limited modifications can be made to a peptide without destroying its biological function. Thus, modification of a peptides of the present invention that does not completely destroy its activity are within the definition of the compound claims as such. Modifications can include, for example, additions, deletions, or substitutions of amino acids residues, substitutions with compounds that mimic amino acid structure or functions, as well as the addition of chemical moieties such as amino or acetyl groups. The modifications can be deliberate or accidental, and can be modifications of the composition or the structure.

An exemplary cell surface receptor envisioned for targeting by a peptide or "modified peptide" of the invention is a member of the integrin receptor family. In an embodiment of the invention, a "modified peptide" may be used to inhibit integrin receptor activity, including, without limitation, the ability of integrin-expressing cells to bind to extracellular matrix proteins and surrounding cells. Modified peptides capable of inhibiting integrin binding/activity have been described in U.S. Pat. Nos. 5,536,814; 5,627,263; 5,912,234; 5,922,676; 5,981,478; 5,912,234; and 6,177,542, the entire contents of each of which is herein incorporated in its entirety by reference.

Retinoids are a class of compounds consisting of four isoprenoid units joined in a head-to-tail manner. All retinoids may be formally derived from a monocyclic parent compound containing five carbon-carbon double bonds and a functional group at the terminus of the acyclic portion. Derivatives of retinoids may be generated by means known to skilled artisans to render the retinoid derivative more therapeutically effective. A retinoid derivative may be, for example, an aldehyde derivative, a carboxylic acid derivative, a substituted derivative, a hydrogenated derivative, or it may be derivatized by functional substitution of a basic hydrocarbon. Retinoid derivatives may, for example, be generated that are more specifically targeted to hyperproliferative cells. As used herein, the term "retinoid derivative" may also be used to refer to a compound or agent having retinoid activity, but which does not necessarily act through a retinoid receptor.

As used herein, the term "biological therapy" refers to a therapeutic regimen designed to enhance a subject's or patient's response to treatment administered to reduce the number of cancer cells and/or symptoms associated with cancer. In general, "biological therapy" involves the use of a variety of cytokines, including, but not limited to, growth factors, interferons, colony stimulating factors, tumor necrosis factors, and interleukins.

As used herein, the term "sensitization" or "sensitizing" refers to treating a subject so as to render the subject or cells therein more susceptible to the effects of a therapeutic regimen; A number of sensitizing agents have been characterized that render cancer cells, for example, more susceptible to therapeutic modalities designed to eradicate cancer from a subject. Such sensitizing agents have been previously described in, for example, U.S. Pat. No. 5,436,337, the entire contents of which is incorporated herein by reference in its entirety.

As used herein, the phrase "disrupting survival signaling from the microenvironment" refers to a situation in which interactions between integrins and their ligands are reduced or decreased. Such interactions may be physically blocked using antibodies or peptides; or may be prevented by decreasing the cell surface expression levels of integrins via transcriptional inhibition; or by blocking survival signaling initiated by integrin receptor ligation by proteins in the microenvironment.

General Description

The present invention relates to the novel finding that increased expression of the alpha-5 beta-1 integrin on metastasized breast cancer cells in the bone marrow transmit a survival signal from matrix proteins in the bone marrow. Ligation of the integrin to fibronectin interrupts integrin-mediated cell death signaling and initiates the cell survival signaling that leads to dormancy, protection from chemotherapy and ultimately relapse in the breast cancer patient. The invention provides for a method to inhibit the expression of the integrin and to interrupt specific elements of the survival pathway that will allow traditional chemotherapy or radiation therapy to be utilized to kill the remaining cells in the bone marrow and avoid a relapse and ultimately resistance by the cells and the death of the patient suffering from a hyperproliferative disorder such as but not limited to breast cancer, or prostate cancer. The over expression of alpha-5 beta-1 is down regulated through the use of kinase or transcription inhibitors such as demonstrated in FIG. 1.

Figure 1:
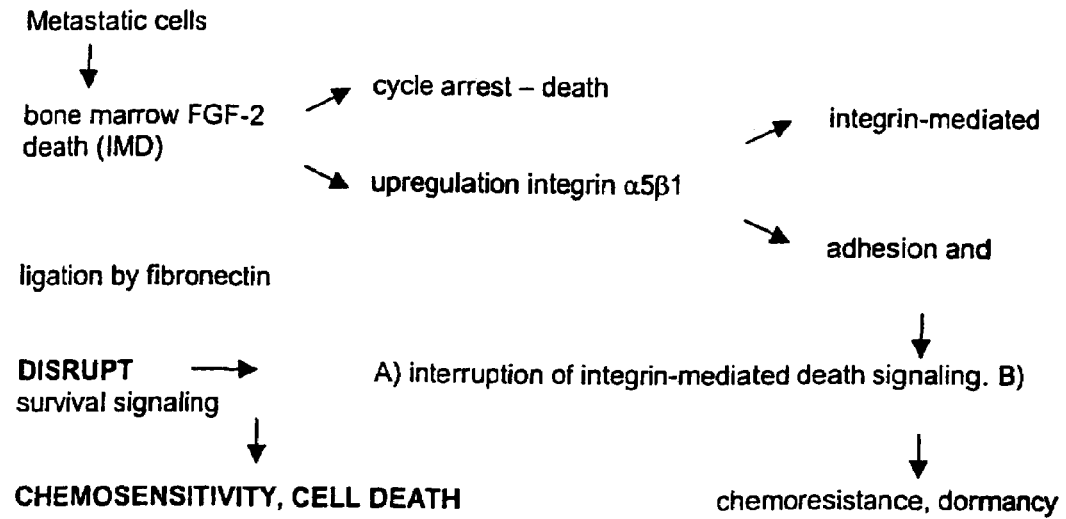
FIG. 1. Breast cancer cells that metastasize to the bone marrow are arrested by deposits of FGF-2 in the bone marrow stroma. FGF-2 induces overexpression of integrins α5 and β1 and leads to massive cell death through unligated or inappropriately ligated integrins by a process termed integrin-mediated death (IMD). Adherence and appropriate ligation of α5β1 on the surviving cells by fibronectin in the stroma interrupts IMD and initiates survival signaling through PI3K. This results in dormancy of the non-cycling sells and protection from cell death induced by cytotoxins. Disruption of the integrin-fibronectin interaction would discontinue survival signaling and initiate IMD. This would render the metastatic cells sensitive to chemotherapy.
Figure 2:
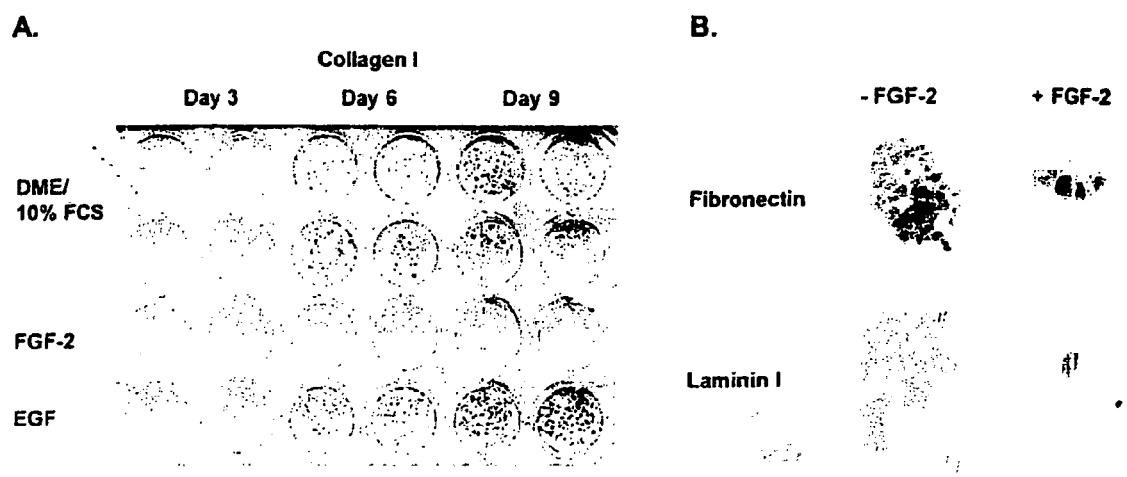
FIG. 2. Survival effects of fibronectin on FGF-2-inhibited breast cancer cells

The schema of FIG. 1 demonstrates the fate of metastatic cells in the bone marrow and the effect of fibronectin ligation through its integrin receptor alpha 5 beta 1 on maintaining survival and chemoresistance. Disruption of this interaction by decreasing synthesis of the integrin or disruption of its interaction with its ligand would allow the cells to become sensitive to chemotherapy and undergo cell death.

In the present invention, evidence is provided which supports a paradigm in which FGF-2 initiates a more differentiated, dormant state in well-differentiated micrometastatic breast cancer cells. This encompasses cell cycle arrest and changes in the integrin repertoire. Cells with improperly ligated integrins such as α5β1, upregulated by FGF-2 in fibroblasts and endothelial cells undergo cell death, likely due to ligand incompatibility. Ligation of integrin α5β1 by fibronectin, a component of bone marrow stroma, which can initiate survival signaling (Matter, M. L, & Ruoslahti, E. (2001) *J. Biol. Chem.* 276, 27757-27763; Lee, J. W. & Juliano, R. L. (2000) *Molecular Biology of the Cell* 11, 1973-1987), promotes survival of FGF-2-responsive cells.

In particular, the present invention is directed to methods for disrupting survival signaling from the microenvironment in cancer cells, wherein said disrupting results in sensitizing cells to chemotherapy, biological therapies or radiation therapy of cancer micrometastases and hyperproliferative disorders in a mammal. The method comprises blocking the interaction of an integrin with an extracellular matrix protein of the microenvironment. A preferred embodiment includes the alpha 5 beta 1 integrin and the preferred extracellular matrix protein is fibronectin. The invention is directed to treating primary tumors, tumor metastasis, micrometastases and hyperproliferative disorders. A further preferred embodiment is treating breast cancer or prostate cancer.

A further preferred embodiment comprises administration of an antibody specific for an integrin or a blocking peptide or modified peptide that disrupts interaction of the integrin with the extracellular matrix. A yet further preferred embodiment comprises administration of all trans retinoic acid or a retinoic acid derivative. A yet further preferred embodiment comprises decreasing expression of cell surface integrins with a transcription inhibitor. The method also comprises treatment with an inhibitor of a kinase, said kinase selected from the group consisting of MEP/MAP kinase, p38, RhoA, Rho kinase, PI3 kinase, PKC, and PKA. The methods further comprise blocking survival signaling initiated by ligation of integrins by microenvironment proteins. The method also comprises use of the inhibitors selected from the group consisting of LY294002, UO126, AG82, Y27632, SB203580, PD169316, PD98059, RO318220, and a C3 transferase inhibitor.

Thus, methods of treating primary cancers, metastatic cancers, micrometastases, and hyperproliferative disorders are encompassed by the present invention. Combination therapy is also envisioned with other standard forms of chemotherapy, radiation therapy and biological therapies and other antineoplastic regimens. It is envisioned that the therapies described in the present invention can be used as adjunct therapy with other anti-neoplastic treatment modalities.

The roles of various stromal proteins and growth factors that are relevant to the bone marrow microenvironment in inducing breast cancer dormancy were studied using a panel of breast cancer cell lines.

To test the potential role of FGF-2 in inducing growth arrest of breast cancer cells in the bone marrow microenvironment, the clonogenic potential of MCF-7, T-47D and MDA-MB-231 breast cancer cells on stromal proteins in the presence of FGF-2 was measured. Clonogenic potential is the ability of single cells to grow into multi-cell clusters, that is a hallmark of metastatic growth of malignant cells. The presence of FGF-2, but not EGF, significantly blocked clonogenic growth of relatively well-differentiated MCF-7 and T-47D cells but had no effect on the highly dedifferentiated aggressive MDA-MB-231 cells. FGF-2 arrested cells failed to survive on collagen-1 and laminin-1, while they survived on fibronectin for many days.

To study the molecular basis for the long-term survival of growth arrested cells, a comparison was made between the expression levels of various integrins in breast cancer cells that remained dormant on fibronectin for 3 and 5 days in the presence of FGF-2, to that of actively growing cells on fibronectin. Microarray analysis showed increased expression levels of the alpha 5 beta 1 integrin, a fibronectin receptor. Western blots demonstrated that FGF-2 induced an increased expression of both the alpha 5 and beta 1 subunits, which together make up the fibronectin receptor in their naturally paired state, in MCF-7 and T-47D cells but had no effect on constitutively very high levels of the alpha 5 subunit in MDA-MB-231 cells. The block in growth of FGF-2-treated cells on fibronectin was further accentuated by pre-treatment of the cells with an anti alpha 5 subunit antibody, strongly suggesting a role for fibronectin in supporting the survival of dormant breast cancer cells in bone marrow. Blocking peptides that disrupt the interaction of fibronectin with its integrin receptor that downregulated the expression of the alpha 5 beta 1 integrin also reversed the survival effects of fibronectin binding to cells in the presence of FGF-2. FGF-2 also induced the phosphorylation of the kinase Akt involved in survival signaling. All trans retinoic acid was able to reverse Akt phosphorylation induced by EGF and reversed FGF-2 induced increases in total and Phosphorylated Akt, suggesting an additional mechanisms of disrupting survival in these cells.

Therapeutic Indications

The administration of kinase or transcription inhibitors or antibodies or blocking peptides or modified peptides as a pre-treatment to sensitize the dormant or metastatic cells for chemotherapy or radiation therapy. The inhibitor could be administered in a variety of methods including but not limited to injectable, oral, liquid, tablet or suppository.

Pharmaceutical Compositions and Methods of Administration

The present invention also provides pharmaceutical compositions used in the method of the invention. Such compositions comprise a therapeutically effective amount of the agents of the present invention, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

The therapeutic agent, whether it be a polypeptide, analog or active fragment-containing compositions or small organic molecules, are conventionally administered by various routes including intravenously, intramuscularly, subcutaneously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of binding capacity desired. Precise amounts of active ingredient required to be administered depend on the judgment of the practitioner and are peculiar to each individual. Suitable regimes for initial administration and subsequent injections are also variable, but are typified by an initial administration followed by repeated doses at intervals by a subsequent injection or other administration.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Administration of the compositions to the site of injury, the target cells, tissues, or organs, may be by way of oral administration as a pill or capsule or a liquid formulation or suspension. It may be administered via the transmucosal, sublingual, nasal, rectal or transdermal route. Parenteral administration may also be via intravenous injection, or intramuscular, intradermal or subcutaneous. Due to the nature of the diseases or conditions for which the present invention is being considered, the route of administration may also involve delivery via suppositories. This is especially true in conditions whereby the ability of the patient to swallow is compromised.

The plant compositions or extracts may be provided as a liposome formulation. Liposome delivery has been utilized as a pharmaceutical delivery system for other compounds for a variety of applications. See, for example Langer (1990) Science 249:1527-1533; Treat et al. (1989) in *Liposomes in the Therapy of Infectious Disease and Cancer*, Lopez-Berestein and Fidler (eds.), Liss: New York, pp. 353-365 (1989). Many suitable liposome formulations are known to the skilled artisan, and may be employed for the purposes of the present invention. For example, see: U.S. Pat. No. 5,190,762.

In a further aspect, liposomes can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier; and the like.

Transdermal delivery of the plant compositions or extracts is also contemplated. Various and numerous methods are known in the art for transdermal administration of a drug, e.g., via a transdermal patch. It can be readily appreciated that a transdermal route of administration may be enhanced by use of a dermal penetration enhancer.

Controlled release oral formulations may be desirable. The plant composition or extract may be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Pulmonary delivery may be used for treatment as well. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Ophthalmic and nasal delivery may be used in the method of the invention. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextrins. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

The compositions and extracts of the present invention are also suited for transmucosal delivery. In particular, the compositions and extracts are particularly suited for sublingual, buccal or rectal delivery of agents that are sensitive to degradation by proteases present in gastric or other bodily fluids having enhanced enzymatic activity. Moreover, transmucosal delivery systems can be used for agents that have low oral bioavailability. The compositions of the instant invention comprise the plant extract dissolved or dispersed in a carrier that comprises a solvent, an optional hydrogel, and an agent that enhances transport across the mucosal membrane. The solvent may be a non-toxic alcohol known in the art as being useful in such formulations of the present invention and may include, but not be limited to ethanol, isopropanol, stearyl alcohol, propylene glycol, polyethylene glycol, and other solvents having similar dissolution characteristics. Other such solvents known in the art can be found in "The Handbook of Pharmaceutical Excipients", published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980).

Any transmucosal preparation suitable for administering the components of the present invention or a pharmaceutically acceptable salt thereof can be used. Particularly, the mixture is any preparation usable in oral, nasal, or rectal cavities that can be formulated using conventional techniques well known in the art. Preferred preparations are those usable in oral, nasal or rectal cavities. For example, the preparation can be a buccal tablet, a sublingual tablet, and the like preparation that dissolve or disintegrate, delivering drug into the mouth of the patient. A spray or drops can be used to deliver the drug to the nasal cavity. A suppository can be used to deliver the mixture to the rectal mucosa. The preparation may or may not deliver the drug in a sustained release fashion.

A specific embodiment for delivery of the components of the present invention is a mucoadhesive preparation. A mucoadhesive preparation is a preparation which upon contact with intact mucous membrane adheres to said mucous membrane for a sufficient time period to induce the desired therapeutic or nutritional effect. The preparation can be a semisolid composition as described for example, in WO 96/09829. It can be a tablet, a powder, a gel or film comprising a mucoadhesive matrix as described for example, in WO 96/30013. The mixture can be prepared as a syrup that adheres to the mucous membrane.

Suitable mucoadhesives include those well known in the art such as polyacrylic acids, preferably having the molecular weight between from about 450,000 to about 4,000,000, for example, Carbopol™934P; sodium carboxymethylcellulose (NaCMC), hydroxypropylmethylcellulose (HPMC), or for example, Methocel™ K100, and hydroxypropylcellulose.

The delivery of the components of the present invention can also be accomplished using a bandage, patch, device and any similar device that contains the components of the present invention and adheres to a mucosal surface. Suitable transmucosal patches are described for example in WO 93/23011, and in U.S. Pat. No. 5,122,127, both of which are hereby incorporated by reference. The patch is designed to deliver the mixture in proportion to the size of the drug/mucosa interface. Accordingly, delivery rates can be adjusted by altering the size of the contact area. The patch that may be best suited for delivery of the components of the present invention may comprise a backing, such backing acting as a barrier for loss of the components of the present invention from the patch. The backing can be any of the conventional materials used in such patches including, but not limited to, polyethylene, ethyl-vinyl acetate copolymer, polyurethane and the like. In a patch that is made of a matrix that is not itself a mucoadhesive, the matrix containing the components of the present invention can be coupled with a mucoadhesive component (such as a mucoadhesive described above) so that the patch may be retained on the mucosal surface. Such patches can be prepared by methods well known to those skilled in the art.

Preparations usable according to the invention can contain other ingredients, such as fillers, lubricants, disintegrants, solubilizing vehicles, flavors, dyes and the like. It may be desirable in some instances to incorporate a mucous membrane penetration enhancer into the preparation. Suitable penetration enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate),and related compounds.

The administration of the compositions and extracts of the present invention can be alone, or in combination with other compounds effective at treating the various medical conditions contemplated by the present invention. Also, the compositions and formulations of the present invention, may be administered with a variety of analgesics, anesthetics, or anxiolytics to increase patient comfort during treatment.

The compositions of the invention described herein may be in the form of a liquid. The liquid may be delivered as a spray, a paste, a gel, or a liquid drop. The desired consistency is achieved by adding in one or more hydrogels, substances that absorb water to create materials with various viscosities. Hydrogels that are suitable for use are well known in the art. See, for example, Handbook of Pharmaceutical Excipients, published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980).

Suitable hydrogels for use in the compositions include, but are not limited to, hydroxypropyl cellulose, hydroxypropyl methyl cellulose, sodium carboxymethyl cellulose and polyacrylic acid. Preferred hydrogels are cellulose ethers such as hydroxyalkylcellulose. The concentration of the hydroxycellulose used in the composition is dependent upon the particular viscosity grade used and the viscosity desired in the final product. Numerous other hydrogels are known in the art and the skilled artisan could easily ascertain the most appropriate hydrogel suitable for use in the instant invention.

The mucosal transport enhancing agents useful with the present invention facilitate the transport of the agents in the claimed invention across the mucosal membrane and into the blood stream of the patient. The mucosal transport enhancing agents are also known in the art, as noted in U.S. Pat. No. 5,284,657, incorporated herein by reference. These agents may be selected from the group of essential or volatile oils, or from non-toxic, pharmaceutically acceptable inorganic and organic acids. The essential or volatile oils may include peppermint oil, spearmint oil, menthol, eucalyptus oil, cinnamon oil, ginger oil, fennel oil, dill oil, and the like. The suitable inorganic or organic acids useful for the instant invention include but are not limited to hydrochloric acid, phosphoric acid, aromatic and aliphatic monocarboxylic or dicarboxylic acids such as acetic acid, citric acid, lactic acid, oleic acid, linoleic acid, palmitic acid, benzoic acid, salicylic acid, and other acids having similar characteristics. The term "aromatic" acid means any acid having a 6-membered ring system characteristic of benzene, whereas the term "aliphatic" acid refers to any acid having a straight chain or branched chain saturated or unsaturated hydrocarbon backbone.

Other suitable transport enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate), and related compounds.

When the compositions and extracts of the instant invention are to be administered to the oral mucosa, the preferred pH should be in the range of pH 3 to about pH 7, with any necessary adjustments made using pharmaceutically acceptable, non-toxic buffer systems generally known in the art.

For topical delivery, a solution of the agent of the invention in water, buffered aqueous solution or other pharmaceutically-acceptable carrier, or in a hydrogel lotion or cream, comprising an emulsion of an aqueous and hydrophobic phase, at a concentration of between 50 μM and 5 mM, is used. A preferred concentration is about 1 mM. To this may be added ascorbic acid or its salts, or other ingredients, or a combination of these, to make a cosmetically-acceptable formulation. Metals should be kept to a minimum. It may be preferably formulated by encapsulation into a liposome for oral, parenteral, or, preferably, topical administration.

The invention provides methods of treatment comprising administering to a subject a therapeutically effective amount of at least one of the agents described herein. In one embodiment, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

The amount of the agent of the invention which is optimal in treating cancers and hyperproliferative disorders can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Treatment Group

A subject in whom administration of the agents of the present invention is an effective therapeutic regiment is preferably a human, but can be any animal. Thus, as can be readily appreciated by one of ordinary skill in the art, the methods and pharmaceutical compositions of the present invention are particularly suited to administration to any animal; particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Furthermore, the administration of the agent may be given at the time of or after the identification of a cancer or hyperproliferative disorder, alone, or in combination with other agents known to be beneficial for ameliorating the symptoms or decreasing tumor load or enhancing the number or activity of immune cells in patients having cancer or a hyperproliferative disorder.

In one embodiment, the subject suitable for treatment by the method of the invention is a subject determined to be suffering from cancer or hyperproliferative disorder. This determination may be made clinically by methods known to one of skill in the art.

EXAMPLES

The following examples are intended to illustrate the invention not limit it.

Example 1

FGF-2 Inhibits Single Cell Growth of Well Differentiated Breast Cancer Cells

MCF-7 and T-47D cells incubated with FGF-2 have markedly diminished clonogenic potential in colony assays in tissue culture on laminin-, collagen I- and IV-coated and uncoated plates (FIGS. 2, 3, 4 and 12). The clones that did form in the presence of FGF-2 were arrested in the 8 cell stage. FGF-2 had no effect on the growth of the highly de-differentiated MDA-MB-231 cells. EFG had no effect and served as a negative control in all three cell types.

Example 2

FGF-2 Induces Expression of Cell Integrins Including Integrin α5 and Restricts Growth of Differentiated Single Breast Cancer Cells Incubation of well differentiated cells with FGF-2 induces the expression of a variety of cell adhesion molecule genes, including α5, α6, β1 and β3, that contribute to cell death when expressed in an unligated state (FIGS. 5, 6, and Tables 1 and 2). FIG. 6 is a Western blot demonstrating induction of integrin α5 expression in MCF-7 and T-47D cells growing on either plastic tissue culture dishes or fibronectin-coated dishes. The increase in integrin α5 expression was assayed for up to five days and remained sustained. No effect is demonstrated on baseline high levels of integrin α5 in MDA-MB-231 cells.

Example 3

Rescue by Fibronectin

Inhibition of colony formation by FGF-2 can be rescued by incubation of cells 6n fibronectin-coated plates (FIGS. 2B, 4, 8, 9, 15 and 16). The protection of colonies in MCF-7 cells treated with FGF-2 was sustained by incubation on fibronectin for up to 15 days (FIG. 8). Fibronectin is a ligand for integrin α5β1 while collagens I and IV are not. These data suggests an association between unligated integrin α5β1 and inhibition of growth and rescue of clonogenic potential by providing a specific ligand for integrin α5β1.

Example 4

Fibronectin Supports Long-Term Survival of FGF-2 Arrested Cells, Potentially Through a P13K Pathway Antibody to integrin α5 inhibits the clonogenic potential of MCF-7 cells on fibronectin both with and without FGF-2 treatments (FIG. 7). Antibody to integrin α3 was used as a negative control. To provide a potential mechanism for survival signaling by integrin α5 on fibronectin in the presence of FGF-2, initial experiments were conducted to determine the phosphorylation of Akt by FGF-2 in the presence of fibronectin. FIG. 10 demonstrates that FGF-2 induced phosphorylation of Akt in MCF-7 and T-47D. Phosphorylation was sustained for the five days of assay; Highly de-differentiated MDA-MB-231 cells, however, express constitutively higher levels of integrin α5 and phospho-Akt, implicating these molecules in their unlimited growth potential on fibronectin.

Example 5

Disruption of Fibronectin/Integrin α5β1 Interaction can Reverse Protection from Cell Death Our data suggest that stromal proteins in the bone marrow microenvironment, such as fibronectin, provide protection of metastatic cancer cells from cell death induced by physiologic factors in the bone marrow microenvironment and from exogenous toxicity such as chemotherapy or radiation therapy. The ability to disrupt the interaction between fibronectin/integrin α5β1 with blocking antibodies to integrin α5 (FIG. 7) and β1 (experiments in progress), peptides to the fibronectin binding site (FIGS. 8, 9 and 14), antisense phosphorothioated oligonucleotides to integrins α5 or β1 or downregulation of integrins α5 or β1 in a dose dependent manner, other transcription inhibitors or retinoids, can result in disruption of the survival signal initiated by fibronectin/integrin α5β1 interaction and thereby become sensitive to chemotherapy and radiation therapy or other biologic therapy-mediated cell death. This approach may sensitize both well-differentiated cells that are non-cycling and dormant in the bone marrow that receive survival protection from ligation to fibronectin in the microenvironment and highly de-differentiated cells that are actively proliferating in the bone marrow that also receive survival signaling from interaction with fibronectin through a constitutively upregulated integrin α5.

Example 6

Disruption of the PI3K/Akt Signal Pathway May Disrupt Support for Breast Cancer Colony Growth by Fibronectin FGF-2-induced phosphorylation of Akt may be disrupted in a number of ways by disrupting the interaction of fibronectin with integrin α5β1 by downregulating the expression of the α5 and β1 subunits, with other transcription factor inhibitors, retinoids, antisense oligonucleotides, disruption of their interaction with blocking antibodies to the integrin α5 β1 or fibronectin, or kinase inhibitors that inhibit activation of PI3K or Akt. Examples of Akt inhibition are shown in FIG. 11, where incubation of MCF-7 cells with ATRA reversed the EGF-mediated phosphorylation of Akt, as demonstrated on a Western blot, and FIGS. 15 and 16 where inhibition of Akt and PI3K, the upstream activation of Akt inhibits survival of dormant clones. This approach may also provide an array of mechanisms for disruptive survival signaling through the PI3K pathway to breast cancer cells at metastatic sites initiated by interaction of integrin α5β1 with fibronectin. Disruption of signaling pathways, kinases and GTPases may disrupt signaling initiated by interaction of fibronectin with the integrins alpha 5 beta 1 in cancer cells that can support survival in these cells. Examples are included which were conducted with inhibitors of Rhp, Rho kinase and MEP/MAp kinase, p38, PKC and PKA resulting in the survival of dormant clones on fibronection (FIGS. 17A and B).

Materials and Methods

Cell Culture

MCF-7, SK-Br-3, MDA-MB-231, PC-3 and LNCaP cells were purchased from the American Type Culture Collection (ATCC), (Rockville, Md.). Cells were cultured in Dulbecco's Modified Eagle's Medium (DMEM) (Gibco BRL, Gaithersburg, Md.) with phenol red 15 mg/l, 2 mM glutamine, 10% heat inactivated fetal calf serum (FCS) and penicillin 50 units/ml and streptomycin 50 micrograms µg/ml (Gemini Bioproducts, Calabasas, Calif.). One to ten thousand cells were incubated on 24 well tissue culture plates that were either commercially coated for tissue culture (uncoated) or coated with 20 g fibronectin, laminin I, collagen I or collagen IV, depending on the cell type or experimental conditions described in the figure legends. Colonies were manually counted at 100× magnification after variable days in culture as described in the figure legends after removing the media and staining cells with crystal violet. Proliferation kinetics were performed as before[1] using 2% trypan blue counts on trypsinized cells on the days indicated in the figure in triplicate plates.

Recombinant human FGF-2 and EGF were purchased from R&D Systems, Minneapolis, Minn.). ATRA was purchased from Sigma. Neutralizing mouse monoclonal antibody to integrin α5 or integrin β3 were purchased from Chemicon, Inc. (Temecula, Calif.). Fibronectin-blocking peptide GRGDSP and control peptides were purchased from American Peptide Co., Inc. (Sunnyvale, Calif.).

Western Blots

Cells were harvested and lysates were prepared as described[2] and analyzed as before[3].

Gene Chip Microarray Analysis

MCF-7 cells were incubated with and without FGF-2 10 ng/ml for 5 days on tissue culture dishes coated with fibronectin 20 μg. Messenger RNA was prepared using solutions provided in a Nonrad GEArray Q series kit and analyzed using a Human Extracellular Matrix and Adhesion Protein chip and a Human Pathway Finder chip (Super Array, Bethesda, Md.).

TABLE 1

Human Extracellular Matrix and Adhesion Molecules GE Array Q series

| Position # on chip | Gene |
|---|---|
| Gene expression upregulated by FGF-2 on fibronectin for 5 days by large multiples | |
| 1. | Meth 1 - A disintegrin-like and metalloprotease (reprolysin type) with thrombospondin type 1 motif, 1 |
| 7. | E-cadherin - cadherin 1, type 1, (epithelial) |
| 12. | Collagen type IV alpha 2 |
| 13. | *Homo sapiens* cystatin C (amyloid angiopathy and cerebral hemorrhage), CST3 |
| 23 | DCC - deleted in colorectal carcinoma |
| 36 | Integrin alpha 5 (fibronectin receptor, alpha polypeptide) |
| 37 | Integrin alpha 6 subunit |
| 47 | Integrin beta 3 (glycoprotein IIIa, antigen CD61) |
| 56 | MUC-18 -*Homo sapiens* MICA gene, allele MUC-18 |
| 62 | MT1-MMP - *Homo sapiens* mRNA for membrane-type matrix metalloprotease 1, MMP14 |
| 69 | MMP26 - *Homo sapiens* matrix metalloprotease-26 mRNA |
| 74 | NCAM1 - Neural cell adhesion molecule 1 |
| 76 | PECAM1 - *Homo sapiens* platelet/endothelial cell adhesion molecule (CD31 antigen) |
| 80 | ELAM-1/E-selectin - human endothelial leukocyte adhesion molecule mRNA |
| 85 | PAI-1 - Plasminogen activator inhibitor, type 1 |
| 94 | TMPRSS$ - Transmembrane protease, serine 4 |
| Gene expression upregulated by FGF-2 on fibronectin for 5 days by small but significant amounts | |
| 20 | Cathepsin D - (lysosomal aspartyl protease) |
| 21 | Cathepsin G - (CTSG) *Homo sapiens* |
| 26 | Fibronectin 1 |
| 33 | Integrin alpha 2b - platelet glycoprotein IIb of IIb/IIIa complex, antigen CD41B |
| 34 | Integrin alpha 3 - antigen CD49C, alpha 3 subunit of VLA-3 receptor |
| 40 | Integrin alpha 9 |
| 44 | Integrin alpha X - (antigen CD11C (p150), alpha polypeptide |
| 48 | Integrin beta 4 |
| 57 | MMP-1 - matrix metalloprotease 1 (interstitial collagenase) |
| 59 | Stromelysin-3, human |
| 61 | MMP-13 - matrix metalloprotease 13 (collagenase 3) |
| 63 | MMP-15 - matrix metalloprotease 15 (membrane inserted) |
| 64 | MMP-16 - matrix metalloprotease 16 (membrane inserted) |
| 65 | MMP-17 - matrix metalloprotease 17 (membrane inserted) |
| 66 | MMP-2 - matrix metalloprotease 2 (gelatinase A, 72 kD gelatinase, 72 kD type IV collagenase) |
| 68 | MMP-24 - matrix metalloprotease 24 (membrane inserted) |
| 75 | NRCAM - neural cell adhesion molecule |
| 86 | SPARC - *Homo sapiens* secreted protein, acidic cysteine-rich (osteonectin) |
| 96 | Vitronectin - serum spreading factor, somatomedin B, complement S protein |

TABLE 2

Human Pathway Finder GE Array Q series

| Position # on chip | Gene |
|---|---|
| Gene expression upregulated by FGF-2 on fibronectin for 5 days by small but significant amounts | |
| 16 | p21$^{WAF1/CIP1}$ - Cyclin-dependent kinase inhibitor 1A (p21, Cip1) |
| Gene expression downgulated by FGF-2 on fibronectin for 5 days by large multiples | |
| 14 | CDC5 - T-cell surface glycoprotein CD5 |
| 19 | p16INK4 - Cyclin-dependent kinase inhibitor 2A (melanoma, p16, inhibits CDK4) |
| Gene expression downregulated by FGF-2 on fibronectin for 5 days by small but significant amounts | |
| 30 | EGR1 - early growth response 1 |
| 31 | EN1 - Engrailed homolog 1 |
| 32 | FASN - fatty acid synthase |
| 41 | Hoxa-1 - *Homo sapiens* homeobox A1 |
| 42 | Hoxb-1 - *Homo sapiens* homeobox B1 |
| 44 | Hsp27 - Heat shock 27 kD protein |
| 45 | Hsp90(CDw52) - Human mRNA for 900 kDa heat-shock protein |

TABLE 3

| Inhibitor | Source | Target | ED50 | Chemical formula |
|---|---|---|---|---|
| UO126 | Calbiochem | MEK1 | 72 nM | 1,4-Diamino-2,3-dicyano-1,4-bis(2-aminophenylthio)butadiene |
| | | MEK2 | 58 nM | |
| AG 82 | Calbiochem | FAK | 7 μM | a-Cyano-(3,4,5-trihydroxy)cinnamonitrile Tyrphostin A25 |
| | | EGFR | | |
| Y-27632 | Calbiochem | Rho kinase | 140 nM | (R)-(+)-trans-N-(4-Pyridyl)-4-(1-aminoethyl)-cyclohexanecarboxamide, 2HCl ROCK Inhibitor |
| SB 203580 | Calbiochem | p38 | 600 nM | 4-(4-Fluorophenyl)-2-(4-methylsulfinylphenyl)-5-(4-pyridyl)1H-imidazole |
| PD169316 | Calbiochem | p38 | 89 nM | 4-(4-Fluorophenyl)-2-(4-nitrophenyl)-5-(4-pyridyl)-1H-imidazole |
| PD 98059 | Calbiochem | MEK | 2 μM | 2-Amino-3-methoxyflavone |
| RO-31-8220 | Calbiochem | Protein kinase C | 10 nM | 3-[1-[3-(Amidinothio)propyl-1H-indol-3-yl]-3-(1-methyl-1H-indol 3-yl)maleimide Bisindolylmaleimide 1X, Methanesulfonate |
| | | Protein kinase A | 900 nM | |
| | | GSK-3 | 2-8-6.8 nM | |
| C3 transferase | Cytoskeleton, Inc | Rho A | 2-5 μg/ml | 24 kD protein* |

*Exoenzyme C3 transferase is an ADP ribosyl transferase that selectively ribosylates Rho proteins on asparagine residue 41, it has extremely low affinity for other members of the Rho family such as Cdc42 and Rac1. ADP ribosylation does not appear to affect the GTPase activity of Rho, rather, it appears to block downstream funtions of the protein. Ribosylation of Rho effectively renders Rho inactive, hence, C3 transferase is a very useful protein in the study of Rho activity.

What is claimed is:

1. A method for disrupting survival signaling from a bone marrow microenvironment to single breast cancer cells or breast cancer cell micrometastases in a mammal with breast cancer, said method comprising administering to said mammal with breast cancer as adjuvant therapy an agent effective in blocking the interaction of an integrin with an extracellular matrix protein of the bone marrow microenvironment or that downregulates expression of said integrin, wherein the integrin is alpha 5 beta 1 and the extracellular matrix protein is fibronectin, and wherein the method results in sensitizing single breast cancer cells or breast cancer cell micrometastases to chemotherapy, biological therapies or radiation therapy of micrometastases in said mammal with breast cancer.

2. The method of claim 1, wherein the agent is selected from the group consisting of an antibody specific for an integrin, a blocking peptide, and a modified peptide effective to disrupt interaction of the integrin with the extracellular matrix.

3. The method of claim 1, wherein the method comprises blocking survival signaling initiated by ligation of alpha 5 beta 1 integrins by microenvironment proteins.

4. A method of inhibiting cellular proliferation or inducing cell death or cellular differentiation of single breast cancer cells or breast cancer cell micrometastases in a mammal with breast cancer or for treating a single breast cancer cell or breast cancer micrometastases in a mammal with breast cancer comprising administering to the mammal with breast cancer as adjuvant therapy an agent capable of downregulating expression of an integrin or blocking the binding of an integrin to an extracellular matrix protein of the bone marrow microenvironment, wherein the integrin is alpha 5 beta 1 and the extracellular matrix protein is fibronectin, and wherein the method results in inhibiting cellular proliferation or inducing cell death or cellular differentiation of the single breast cancer cell or breast cancer cell micrometastases or in treating the single breast cancer cell or breast cancer cell micrometastases in the mammal with breast cancer.

5. The method of claim 4, comprising administering an antibody effective to block integrin alpha 5 beta 1 or a peptide effective to block fibronectin or a modified peptide effective to block fibronectin, or any combinations thereof, wherein the antibody or peptide is administered prior to or concurrent with a chemotherapeutic agent or radiation therapy.

6. The method of claim 4, wherein the method results in sensitizing to, or potentiating chemotherapy or radiation therapy in mammals undergoing treatment for breast cancer.

7. The method of claim 1, wherein the mammal with breast cancer is a human.

8. The method of claim 4, wherein the mammal with breast cancer is a human.

* * * * *